US006872398B2

(12) United States Patent
Castric et al.

(10) Patent No.: US 6,872,398 B2
(45) Date of Patent: *Mar. 29, 2005

(54) CONJUGATE VACCINE AGAINST GRAM-NEGATIVE BACTERIAL INFECTIONS

(75) Inventors: Peter Castric, Pittsburgh, PA (US); Alan S. Cross, Chevy Chase, MD (US); Jerald C. Sadoff, Washington, DC (US)

(73) Assignee: The United States of America as represented by the Secretary of the Army, Washington, DC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/337,393

(22) Filed: Jun. 23, 1999

(65) Prior Publication Data

US 2002/0039755 A1 Apr. 4, 2002

Related U.S. Application Data

(62) Division of application No. 08/576,974, filed on Dec. 22, 1995, now abandoned.

(51) Int. Cl.[7] .............................................. A61K 39/02
(52) U.S. Cl. ................. 424/242.1; 424/200.1; 424/190.1; 424/256.1; 424/260.1; 530/350; 435/69.3; 435/71.2; 435/91; 435/170.3; 435/252.3; 435/244.1; 435/256.1
(58) Field of Search ................ 424/200.1, 242.1, 424/190.1, 260.1, 244.1, 256.1; 435/69.3, 71.2, 91, 170, 172.3, 252.2, 252.3; 530/350, 388.2; 514/53

(56) References Cited

U.S. PATENT DOCUMENTS

| 3,674,863 A | * | 7/1972 | Fisher et al. | 424/92 |
| 4,696,896 A | * | 9/1987 | Brinton et al. | 435/7 |
| 4,737,363 A | * | 4/1988 | Stewart et al. | 424/94.63 |

(Continued)

FOREIGN PATENT DOCUMENTS

| EP | 048422 | * | 9/1981 | |
| WO | 86/02557 | * | 5/1986 | C12P/21/00 |
| WO | 90/11777 | * | 10/1990 | |
| WO | 90/13563 | * | 11/1990 | |
| WO | 92/12169 | * | 7/1992 | |
| WO | 93/11791 | * | 6/1993 | C12N/1/00 |
| WO | 94/08021 | * | 4/1994 | C12N/15/61 |

OTHER PUBLICATIONS

Lepper, A.W.D. et al, Veterinary Microbiology, vol. 36,(1–2) pp. 175–193, Jul. 1993.*

(Continued)

*Primary Examiner*—Lynette R. F. Smith
*Assistant Examiner*—Ginny Allen Portner
(74) *Attorney, Agent, or Firm*—Elizabeth Arwine; Charles H. Harris

(57) ABSTRACT

The present invention relates to a broadly reactive vaccine against Gram-negative bacteria which is composed of a biological glycan-pilus conjugate. The conjugate core is a common pilus type to which is attached the glycan of choice in vivo. Pooling of these bioconjugates produces a multivalent vaccine. These pili give high bronchial titers when delivered by the intranasal route. Mice vaccinated with pure glycosylated *P. aeruginosa* strain 1244 pili in this manner are protected against respiratory challenge with *P. aeruginosa* strain 1244. The present invention further relates to a DNA and amino acid sequence of a new gene, pilO, which is capable of glycosylating pilin of Gram-negative bacteria and uses thereof.

6 Claims, 7 Drawing Sheets

U.S. PATENT DOCUMENTS

| | | | | | |
|---|---|---|---|---|---|
| 4,769,240 | A | * | 9/1988 | Brinton | 424/92 |
| 4,788,056 | A | * | 11/1988 | Lutticken et al. | 424/89 |
| 4,971,794 | A | * | 11/1990 | Linggood et al. | 424/92 |
| 5,153,312 | A | * | 10/1992 | Porro | 530/405 |
| 5,223,604 | A | * | 6/1993 | Hodges et al. | 530/327 |
| 5,288,617 | A | * | 2/1994 | Mattick et al. | 435/69.3 |
| 5,370,872 | A | * | 12/1994 | Cryz et al. | 424/194.1 |
| 5,494,672 | A | * | 2/1996 | Hodges et al. | 424/260.1 |
| 5,595,744 | A | * | 1/1997 | Chalmers et al. | 424/253.1 |
| 5,612,036 | A | * | 3/1997 | Hodges et al. | 424/190.1 |
| 5,705,161 | A | * | 1/1998 | Van Der Ley et al. | 424/250.1 |
| 5,804,198 | A | * | 9/1998 | Lindberg et al. | 424/242.1 |
| 5,834,591 | A | * | 11/1998 | Normark et al. | 530/350 |
| 5,874,088 | A | * | 2/1999 | Mekalanos | 424/200.1 |
| 5,955,080 | A | * | 9/1999 | Reilly et al. | 424/194.1 |
| 5,994,072 | A | * | 11/1999 | Lam et al. | 435/6 |
| 6,399,074 | B1 | * | 6/2002 | Roland | 424/200.1 |
| 6,436,653 | B1 | * | 8/2002 | Jakobsen et al. | 435/7.35 |

OTHER PUBLICATIONS

Hunt, J.D et al, Vaccine, vol. 12(5), pp. 457–464, Apr. 1994.*

Saiman, L et al, Infection Immunity, vol. 57(9), pp. 2764–2770, Sep. 1989.*

Gbarah, A et al, Infection Immunity, vol. 61(5), pates 1687–1693, May 1993.*

Castric, PA et al, Molecular and general genetics, vol. 216(1), pp. 75–80, (abstract), Mar. 1989.*

Castric, PA et al, Infection Immunity, vol. 62(2), pp. 371–376, Feb. 1994.*

Stimson, E et al, Molecular Microbiology, Sep. 1995, vol. 17(6), pp. 1201–1214, Sep. 1995.*

Virji, M et al, Molecular Microbiology, Dec. 1993, vol. 10(5), pp. 1013–1028, Dec. 1993.*

Wu, X et al, Current Eye Research, Oct. 1995, vol. 14(10), pp. 969–967 (abstract only), Oct. 1995.*

Ishimoto, KS et al, PNAS (USA), vol. 86, pp. 1954–1957, Mar. 1989.*

Lepper, AWD et al, Veterinary Medicine, vol. 36(1–2), pp. 175–183, Jul. 1993.*

Russell, MA et al, Molecular Microbiology, vol. 13(6), pp. 973–985, Sep. 1994.*

Saiman, L et al, Mar. 1990, vol. 161(3), The Journal of Infectious Diseases, pp. 541–548.*

Cryz, SJ et al, Contributions to microbiology and immunology, vol. 10, 1989, pp. 166–189, Conjuate vaccines against Pseudomonas aeruginosa and malaria.*

Castric, P., PilO, a gene required for glycosylation of Pseudomonas aeruginosa 1244 pilin, Microbiology, 1995, vol. 141, No. 5, pp. 1247–1254. See entire document.

Radhakrishnan, L., Identification of Stimuli that Affect the Expression of pilA, the pilin structural gene in Pseudomonas aeruginosa 1244, Masters Thesis, Duquesne University, 1995, see pag10.

Davis, S.A., Comprison of heterologous pili production in Pseudomonas aeruginosa PA103 and 1244 and development of a method for purification of PA103 pili, Masters Thesis, Duquesne University, 1993. pp. 1–49.

* cited by examiner

```
                                                      pilO
1244:  TTTCTGGATTCAGGGTTGGATTCCCATGTGAGGGGAATATCGGTTGAAATCCGGCTGTG
        · ·  ·· ··  ·   ·· ··       · ·  ·           ·   ·  ·  ·
PA103: AATGAGCCTTAATAGCTGTTTTTGTTGATTGGTGTCGATCGGTATTGAGATCATTCCAG
        pilA
```

```
                                   tRNA
1244:  CCGAGTGATACCTTCCCCGCGCCGCCGGATTAGCTCA
        ·· ········· ··  ·····················
PA103: TTGACTGATACCTTACCGCCGCCGCCGGATTAGCTCA
```

```
1244:  GTCGGTAGAGCAGCTCATTCGTAATGAGAAGGTCGGGGGTTCGATTCCTCTATCCGGCA
       ·······················································
       ·······················································
PA103: GTCGGTAGAGCAGCTCATTCGTAATGAGAAGGTCGGGGGTTCGATTCCTCTATCCGGCA
```

```
1244:  CCAGTCGCAATAAAAAGCCCCGCTTCGGCGGGGCTTT
           ────→           ←────
       ·····································
       ·····································
PA103: CCAGTCGCAATAAAAAGCCCCGCTTCGGCGGGGCTTT
```

```
           ←────
1244:  TTATTGCCTGCGATTCGTTCAGAGGGGGTGAGGCGCATGGACAGGTCGACGGCCCTGAC
       ···········································································
       ···········································································
PA103: TTATTGCCTGCGATTCGTTCAGAGGGGGTGAGGCGCATGGACAGGTCGACGGCCCTGAC
```

```
1244:  ATCCTTGGTCAGGGTGCCGATGGAGATGTAGTCGACG
       ···················· ·· ····
       ···················· ·· ····
PA103: ATCCTTGGTCAGGGTGCCGATGGAGATCTACTCGAGC
```

```
1244:  CCGGTCTCGGCGATGTTGCGCAGGGGGTGCCCTCGTTGATCC-GCCGGAAGCTT
       ···························· ·········· ··········
       ···························· ·········· ··········
PA103: CCGGTCTCGGCGATGTTGCGCAGGGGGTGCTTTCGTTGATCCCGCCGGAAGCTT
```

Fig. 1

1   2
8.0 ▶
6.0 ▶
4.0 ▶
Fig. 4B

CONJUGATE VACCINE AGAINST GRAM-NEGATIVE BACTERIAL INFECTIONS

This application is a continuation division of application Ser. No. 08/576,974, filed Dec. 22, 1995, now abandoned.

Pseudomonas aeruginosa is recognized as a leading cause of life-threatening infection among compromised patient populations in hospitals. Cancer patients, and patients with burn wounds, cystic fibrosis, acute leukemia, organ transplants, and intravenous-drug addiction are particularly susceptible to acquiring a serious P. aeruginosa infection. The most serious infections include pneumonia, septicemia, malignant-external otitis, and meningitis. The mortality rate for such infections can exceed 50%, and is usually the highest for any bacterial pathogen (Cryz, S. J., Jr. In Pseudomnonas aeruginosa as an Opporunistic Pathogoen, Mario Campa etal., Eds. Plenum Press, New York, 1993, pp. 383–395. All documents cited herein infra and supra are hereby incorporated by reference thereto).

Therapy for the management of severe P. aeruginosa infections has been a problem for many years due to the debilitated condition of the patient and the high frequency of multiple antibiotic resistance of clinical isolates of this bacteria. Immunotherapy has been explored as an alternative. In this area, attention has focused on the virulence factors of P. aeruginosa. As with other bacterial pathogens, virulence of P. aeruginosa is multifactorial and is the product of many interacting factors involving both the bacterium and the human host.

P. aeruginosa is an opportunistic pathogen, therefore, a key component of this bacterium's pathogenicity is the ability of the microorganisms to adhere to epithelial cells of mucosal surfaces (E. H. Blackey, 1981, J. Infect. Dis. 143: 325–345). The somatic pili of P. aeruginosa, protein filaments clustered around the flagellum and extending from the cell surface, have been implicated in adherence to host tissue (Ramphal et al., 1984, Infect. Immun. 44: 38–40; Woods et al., 1980, Infect. Immun. 29: 1146–1151). Pili are composed of monomeric subunits, pilin, which have a molecular weight of 15–18000 daltons (Frost and Paranchych, 1977, J. Bacteriol. 131: 259–269; Sastry et al. ,1983, FEBS Lett 151: 253–256; Sastry et al. ,1985, J. Bacteriol. 164:571–577) and are arranged in a helical fashion within the pilus fiber (Watts et al. ,1983, Biochemistry 22: 3640–3646). The pilins of P. aeruginosa are similar in structure and function to those produced by many Gram-negative bacteria such as species of the genera Dichelobacter(Elleman, T. C. 1988 Microbiol. Rev. 52:233–247), Eikenella (Rao and Progulske-Fox, 1993 J. Gen. Microbiol. 139: 651–660), Kingella (Weir and Marrs, 1992, Infect. Immun. 60: 3437–3441), Moraxella (Marrs et al. 1985, J. Bacteriol. 163: 132–139), Neisseria (Meyer et al., 1984, Proc. Natl. Acad. Sci. USA 81: 6110–6114), and Vibrio (Faast etal., 1989, Gene 85: 227–231).

In P. aeruginosa, pilin is encoded by a single chromosomal copy (Pasloske et al., 1985, FEBS Lett. 183: 408–412; Sastry et al., 1985, J. Bacteriol. 164: 571–577), the pilA gene. The nucleotide sequence of several P. aeruginosa pilA genes is known and comparisons of deduced pilin primary structure and flanking DNA sequence have shown characteristic variation which allows differentiation of P. aeruginosa pilins into at least two groups, group I (such as pili strain 1244) and group II pilins (PA 103, T2A, PAO, PAK pilins) (Castric and Deal, 1994, Infect. Immun. 62: 371–376). This pilus grouping is further supported by nucleotide sequence homology of the regions flanking the pilA gene. A surprising feature of this work was the discovery that group I pilin determinants were relatively common (58/95 and include different strains of different immunotypes as determined by polyclonal antibody reaction) among clinical isolates. These results indicate that group I pili represent a major clinical serogroup from which potential components of an anti-pilus vaccine with broad specificity may be obtained.

The use of P. aeruginosa pili as a vaccine presents many advantages. Unlike previous lipopolysaccharide-based Pseudomonas vaccines, pili produce minimal side effects and are well known to be immunogenic in humans, possibly due to antigen organization (Bachman, et al., 1993, Science 262: 1448–1451) brought about by subunit arrangement in the fiber. Much is known of the biochemistry and molecular biology of the pili and the technology is available for the identification and characterization of pilus epitopes. Pili can be prepared easily in homogeneous form and methods described in this application allow large scale production of pili which are compatible with modern forms of vaccine delivery such as microencapsulation. The P. aeruginosa pili can be engineered to act as "carriers" for other protein epitopes, thereby conferring the advantages of pili to other antigens; DNA sequences coding for known protein epitopes (outer membrane proteins for example) could be used to replace known surface pilin epitopes by PCR methodologies. The advantages of peptide technology can be applied to pilus vaccines. Cocktails of peptide epitopes can be constructed to deal with antigenic variation seen in serotype populations.

SUMMARY OF THE INVENTION

The present invention relates to a pilus-based vaccine and is based on recent work showing that pili from group I strains of P. aeruginosa, a clinically common group, are glycosylated and that pili glycosylation may be involved in specific or nonspecific adhesion to the host cell independent of pilin protein-mediated attachment (Castric, P. ,1995, Microbiology 141: 1247–1254). Glycosylated pili are shown to produce high bronchial titers when delivered by the intranasal route. Mice vaccinated with pure P. aeruginosa strain 1244 pili in this manner are protected against respiratory challenge with P. aeruginosa strain 1244.

More specifically, the present invention relates to a new gene sequence, pilO, the product of which glycosylates the pili of P. aeruginosa strains by adding the specific O-antigen subunits of the lipopolysaccharide (LPS) carried by that strain onto the pili resulting in antigenic glycosylated pili useful as a vaccine against infection with that strain.

Nucleotide sequencing of a region downstream from the pilin structural gene (pilA) of P. aeruginosa strain 1244 (a group I strain), revealed an open reading frame (ORF) potentially able to code for another protein. This ORF, called pilO, was flanked by a tRNA$^{thr}$ gene, which was followed by a transcriptional termination sequence. The tRNA$^{thr}$ gene and the termination sequence were nearly identical to sequences found immediately adjacent to the pilA gene of several P. aeruginosa strains. A 2200 base mRNA strand, which contained both the pilO and pilA transcripts, was prodcuced from this region, while 650 base transcript containing only pilA was present in a 100-fold excess over the longer transcript. Hyperexpression of the pilA gene in a pilO⁻ strain resulted in normal pilus-specific phage sensitivity and twitching motility, two other functions of pili. The pilin produced by this strain however had a lower apparent Miv and a more neutral pI compared to that produced by a strain containing a functional pilO gene. This pilin failed to react with a sugar-specific reagent which recognized pilin produced by the strain containing a functional pilO gene (Castric, P.,1995, *Microbiology* 141: 1247–1254).

Experiments have shown that pilO is specific for strain 1244 pilin. For example, strain 1244 will produce strain PA 103 pili (a group II pilin) from a plasmid carrying the cloned gene, but will not glycosylate the PA 103 pilin protein. However, pilO is not specific for the O-antigen attached to the strain 1244 pilin. pilO will glycosylate strain 1244 pili with the LPS O-antigen repeating units of other *P. aeruginosa* strains. For example, strain PAK (another group II strain), carrying a plasmid retaining both the pilO gene and strain 1244 pilin gene, will produce strain 1244 pili carrying the chemically and serologically distinctive strain PAK O-antigen. In fact, the potential for O-antigen range of glycosylation is extremely wide and can extend to virtually any Gram-negative bacterium, *P. aeruginosa* and other species.

The recent discovery of pilin glycosylation allows the design of vaccines specific for different strains of *P. aeruginosa*, or of Gram-negative bacteria, by the addition to the pilin core of the specific glycan produced in the bacteria for which a vaccine is desired and using the resulting pili as a vaccine. Other vaccines presently being studied are composed of the LPS associated with the O-antigen. The use of an LPS based vaccine has several serious drawbacks as compared to the use of glycosylated pili as a vaccine. Glycosylated pili contain the immunogenic portion (O-antigen) but not the toxic part (lipid A) of the LPS molecule resulting in a safer, better tolerated vaccine. The range of protection of a cocktail of glycosylated pili will be broader than a cocktail of LPS due to the common epitopes of the pilus protein. Protection will be both pilus based and O-antigen based. LPS purification is time consuming, expensive and difficult. Glycosylated pili can be produced in large amounts by a new method described in this application involving the use of broth cultures instead of the commonly used agar cultures. Purification of glycosylated pili is quickly accomplished, inexpensive, and requires only common laboratory procedures.

The design of a pilus vaccine and understanding the immunological relationship among native pili is dependent on the ability to determine which parts of the pilus surface make up the B-cell epitopes. The positions of the protein B-cell epitopes of the native strain 1244 pili were determined using the Geysen tethered peptide pin assay as described in Castric and Deal, 1994, supra. Four epitope regions were revealed representing the portions of the pilin primary structure which occupy the surface of the pilus fiber. These sequences would be important in peptide vaccine design. Two of these sequences, region (SEQ ID NO: 3) and region 4 (SEQ ID NO: 4) may also represent glycosylation recognition sequences according to recent results from peptide mapping of PilA.

Therefore, it is an object of the present invention to provide a pilO DNA fragment encoding 1386 nucleotides useful as a glycosylation sequence for 1244 pilin protein in the production of a diagnostic agent and a vaccine.

It is another object of the present invention to provide a pilO DNA fragment useful as a glycosylation sequence for pilin of other gram negative bacteria. The pilO protein is capable of glycosylating any protein which contains the pilin glycosylation recognition sequence. The sequence can be incorporated in several ways, for example, using PCR methods, the pilin glycosylation recognition sequence can be inserted into a gene of a known surface protein; this engineered gene can be incorporated into the chromosome of the host by gene replacement, and pilO hyperexpressed from a broad host range plasmid such as pPAC46 which grows and functions in nearly all Gram-negative bacteria.

It is another object of the present invention to provide an amino acid sequence for pilO protein encoding 461 amino acids.

It is another object of the invention to provide a recombinant vector comprising a vector and the above described DNA fragment.

It is another object of the invention to provide a recombinant vector comprising a vector and the above described DNA fragment functionally positioned next to a pilin gene, preferably the pilin gene of strain 1244.

It is a further object of the present invention to provide a host cell transformed with any of the above-described recombinant DNA constructs.

It is another object of the present invention to provide a method for producing pilO protein which comprises culturing a host cell under conditions such that a recombinant vector comprising a vector and the pilO DNA fragment is expressed and pilO protein is thereby produced, and isolating pilO protein for use as a glycosylation agent.

It is yet a further object of the invention to provide a method for producing glycosylated pilin or a pilin-glycan conjugate which comprises culturing a host cell under conditions such that the above-described DNA fragment is expressed and glycosylated pilin is produced, and isolating glycosylated pilin for use as a vaccine and diagnostic agent.

It is still another object of the invention to provide a purified pilO protein useful as a glycosylating agent.

It is a further object of the present invention to provide an antibody to the above-described glycosylated pilin for use as a therapeutic agent and a diagnostic agent.

It is yet another object of the invention to provide a *P. aeruginosa* vaccine comprising a pilin-glycan conjugate effective for the production of antigenic and immunogenic response resulting in the protection of a mammal against *P. aeruginosa* infection.

It is a further object of the invention to provide a multivalent Gram-negative vaccine comprising glycosylated pilins from a variety of strains or species of Gram-negative bacteria effective for the production of antigenic and immunogenic response resulting in the protection of a mammal infection with Gram-negative bacilli.

It is yet another object of the present invention to provide a method for the diagnosis of *P. aeruginosa* infection comprising the steps of:

(i) contacting a sample from an individual suspected of having the infection with antibodies which recognize glycosylated pilin or an attached glycan of *P. aeruginosa*; and (ii) detecting the presence or absence of a complex formed between *P. aeruginosa* and antibodies specific therefor.

It is yet another object of the present invention to provide a method for the diagnosis of Gram-negative bacterial infection comprising the steps of:

(i) contacting a sample from an individual suspected of having the disease with antibodies which recognize glycosylated pilin or an attached glycan of Gram-negative bacteria; and (ii) detecting the presence or absence of a complex formed between *P. aeruginosa* and antibodies specific therefor.

It is yet another object of the present invention to provide a method for the diagnosis of P. aeruginosa from a sample using the polymerase chain reaction, said method comprising:

(I) extracting DNA from the sample;

(ii) contacting said DNA with
   (a) at least four nucleotide triphosphates,
   (b) a primer that hybridizes to pilO DNA, and
   (c) an enzyme with polynucleotide synthetic activity,
under conditions suitable for the hybridization and extension of said first primer by said enzyme, whereby a first DNA product is synthesized with said DNA as a template therefor, such that a duplex molecule is formed;

(iii) denaturing said duplex to release said first DNA product from said DNA;

(iv) contacting said first DNA product with a reaction mixture comprising:
   (a) at least four nucleotide triphosphates,
   (b) a second primer that hybridizes to said first DNA, and
   (c) an enzyme with polynucleotide synthetic activity,
under conditions suitable for the hybridization and extension of said second primer by said enzyme, whereby a second DNA product is synthesized with said first DNA as a template therefor, such that a duplex molecule is formed;

(v) denaturing said second DNA product from said first DNA product;

(vi) repeating steps iii–vi for a sufficient number of times to achieve linear production of said first and second DNA products;

(vii) fractionating said first and second DNA products generated from said pilO DNA; and (viii) detecting said fractionated products for the presence or absence of pilO in a sample.

It is yet another object of the present invention to provide a method for the detection of P. aeroginosa in a sample which comprises assaying for the presence or absence of pilO RNA or DNA in a sample by hybridization assays.

It is a further object of the present invention to provide a diagnostic kit comprising a glycosylated pilin antibody and ancillary reagents suitable for use in detecting the presence P. aeruginosa in mammalian tissue or serum.

It is another object of the present invention to provide a diagnostic kit comprising antibodies against glycosylated pilins of Gram-negative bacteria and ancillary reagents suitable for use in detecting the presence of Gram-negative bacteria in mammalian tissue of serum.

It is a further object of the present invention to provide a diagnostic kit comprising primers specific for the amplification of pilO sequences and ancillary reagents suitable for use in detecting the presence P. aeruginosa in mammalian tissue or serum.

It is yet an object of the present invention to provide a therapeutic method for the treatment or amelioration of symptoms of P. aeruginosa and other species of Gram-negative bacilli, said method comprising providing to an individual in need of such treatment an effective amount of sera from individuals immunized with one or more pilin-glycan conjugate(s) in a pharmaceutically acceptable excipient.

It is further another object of the present invention to provide a therapeutic method for the treatment or amelioration of symptoms of Gram-negative infection, said method comprising providing to an individual in need of such treatment an effective amount of antibodies against the pilin-glycan conjugate or attached glycan of the Gram-negative bacteria thereby inhibiting the adhesion and colonization of the bacteria in the host in a pharmaceutically acceptable excipient.

It is another object of the present invention to provide a therapeutic method for the treatment or amelioration of symptoms of Gram-negative infection, said method comprising providing to an individual in need of such treatment an effective amount of glycosylated pili from a variety of strains or species of Gram-negative bacteria in order to inhibit adhesion of bacteria to a host cell.

It is yet another object of the present invention to provide a method for large scale production of pilin, either glycosylated or unglycosylated, for use as a vaccine and a diagnostic agent.

It is still another object of the present invention to provide antigenic epitopes of pilA, the pilin core protein, which are useful in peptide vaccine design.

BRIEF DESCRIPTION OF THE DRAWINGS

These and other features, aspects, and advantages of the present invention will become better understood with reference to the following description and appended claims, and accompanying drawings where:

FIG. 1 shows sequence homology of the region downstream from the pilO gene (SEQ ID NO:5), with the region downstream of the pilA gene of P. Aeruginosa strain PA 103 (SEQ ID NO:6) (Johnson et al., 1986, *J. Biol. Chem.* 261: 15703–15708). Colons indicate base homology. Regions containing significant dyad symmetry are indicated by opposing arrows. The tRNA gene region is highlighted.

DETAILED DESCRIPTION

Figure 2:
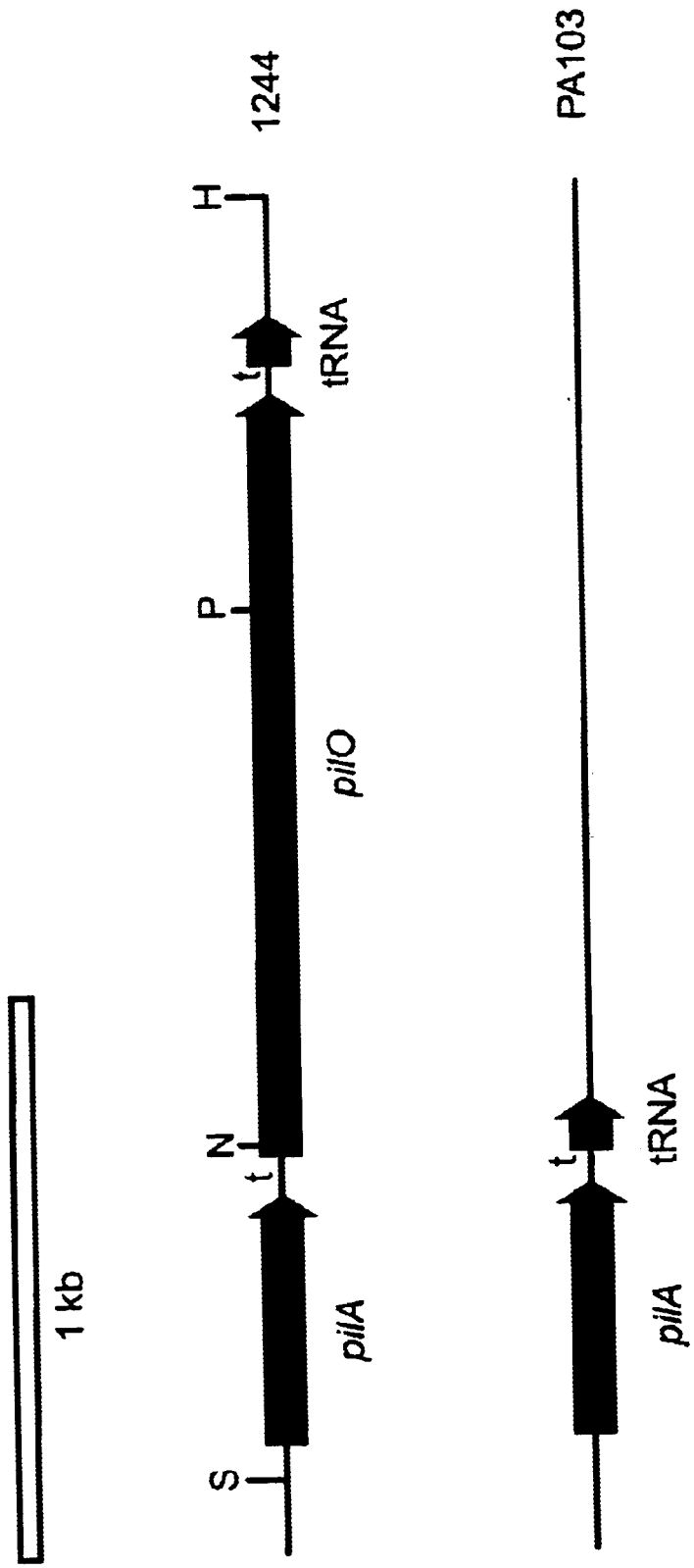
FIG. 2 shows a comparison of the pilin gene regions of P. aeruginosa strain 1244 and strain PA 103. Potential transcriptional stops are indicated by the letter "t". Restriction endonuclease sites are H, HindIII; N, NheI; P, PstI; S, SphI.

In one embodiment, the present invention relates to a DNA or cDNA segment which encodes pilO, a glycosylation sequence of pilA pilin core protein. The sequence of the gene, specified in SEQ ID NO: 1, was obtained by sequencing a region downstream from the *P. aeruginosa* 1244 pilA gene. The sequenced gene fragment comprising 1386 nucleotides of open reading frame with a 60.1% G+C content consistent with the general range given for *P. aeruginosa* chromosomal DNA.

DNA or polynucleotide sequences to which the invention also relates include sequences of at least about 6 nucleotides, preferably at least about 8 nucleotides, more preferably at least about 10–12 nucleotides, most preferably at least about 15–20 nucleotides corresponding, i e., homologous to or complementary to, a region of the pilO nucleotide sequence. Preferably, the sequence of the region from which the polynucleotide is derived is homologous to or complementary to a sequence which is unique to the pilO gene. Whether or not a sequence is unique to the pilO gene can be determined by techniques known to those of skill in the arL For example, the sequence can be compared to sequences in databarnks, e.g., Genebank. Regions from which typical DNA sequences may be derived include but are not limited to, for example, regions encoding specific epitopes, as well as non-transcribed and/or non-traslated regions.

The derived polynucleotide is not necessarily physically derived from the nucleotide sequence shown in SEQ ID NO:1, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays and for the discovery of other pilO sequences.

In another embodiment, the present invention relates to a recombinant DNA molecule that includes a vector and a DNA sequence as described above. The vector can take the form of a plasmid such as any broad host range expression vector for example pMMB66EH and others known in the art.

In a further embodiment, the present invention relates to host cells stably transformed or transfected with the above-described recombinant DNA constructs. The host cell can be any Gram-negative bacteria for which glycosylated pilin is desired. The vector containing the pilO gene is expressed in the bacteria and the product of the pilO gene is able to add subunits of the specific O-antigen of the host bacteria to the core pilin producing glycosylated pilins which can be isolated for use as a vaccine and in diagnostic assays. For example, the plasmid pPAC46, described below in Materials and Methods, containing both the pilA and pilO wherein the pilA gene of strain 1244 was placed downstream from the sac promoter (in such a way as to inactivate the pilA promoter) of the broad host range expression vector pMMB66EH (Furste, et al., 1986, Gene 48: 119–131) results in high levels of glycosylated pilus production by hyperexpression of the pilA gene. Promoters other than the tac promoter include λ $P_L$ promoter, T7 promoter, and MalE promoter. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. The DNA sequence can be present in the vector operably linked to a highly purified IgG molecule, an adjuvant, a carrier, or an agent for aid in purification of glycosylated pilin. The transformed or transfected host cells can be used as a source of DNA sequences described above. When the recombinant molecule takes the form of an expression system, the transformed or transfected cells can be used as a source of the protein described below.

In another embodiment, the present invention relates to a pilO protein having an amino acid sequence corresponding to SEQ ID NO: 2 and encompassing 461 amino acids or any allelic variation thereof.

A polypeptide or amino acid sequence derived from the amino acid sequence in SEQ ID NO:2, refers to a polypeptide having an amino acid sequence identical to that of a polypeptide encoded in the sequence, or a portion thereof wherein the portion consists of at least 2–5 amino acids, and more preferably at least 8–10 amino acids, and even more preferably at least 11–15 amino acids, or which is immunologically identifiable with a polypeptide encoded in the sequence.

A recombinant or derived polypeptide is not necessarily translated from a designated nucleic acid sequence, or the sequence in SEQ ID NO:1; it may be generated in any manner, including for example, chemical synthesis, or expression of a recombinant expression system. In addition the polypeptide can be fused to other proteins or polypeptides for example, MalE protein for transport into the periplasm or for secretion from the cell.

In a further embodiment, the present invention relates to a method of producing glycosylated pilin which includes culturing the above-described host cells, under conditions such that the DNA fragment is expressed and a glycan specific for such host cells is added to the core pilin protein producing glycosylated pilin. The glycosylated pili can then be isolated using methodology well known in the art or by the new large scale production method described below. The glycosylated pili can be used as a vaccine for immunity against infection with the host bacteria or as a diagnostic tool for detection of host bacterial infection. The transformed host cells can be used to analyze the effectiveness of drugs and agents which inhibit adhesion of host bacteria to cells, such as host proteins or chemically derived agents or other proteins which may interact with the bacteria to downregulate or alter the expression of piO or affect the ability of pili to adhere to cells. A method for testing the effectiveness of a drug or agent capable of inhibiting the adhesion of the Gram-negative bacteria being studies can be for example the adhesion assay of Deal and Krivan, *Met. Enzymol.* 236: 346–353.

In another embodiment, the present invention relates to antibodies specific for the above-described glycosylated pili. For instance, an antibody can be raised against the complete glycosylated pili or against a portion thereof. Persons with ordinary skill in the art using standard methodology can raise monoclonal and polyclonal antibodies to the pili (or polypeptide) of the present invention, or the specific O-glycan attached to the pilin, or a unique portion of the pilin. Material and methods for producing antibodies are well known in the art (see for example Goding, in, *Monoclonal Antibodies: Principles and Practice*, Chapter 4, 1986). In addition, the protein or polypeptide can be fused to other proteins or polypeptides which increase its antigenicity, thereby producing higher titers of neutralizing antibody when used as a vaccine. Examples of such proteins or polypeptides include any adjuvants or carriers safe for human use, such as aluminum hydroxide.

In a further embodiment, the present invention relates to a method of detecting the presence of Gram-negative bacterial infection or antibodies against Gram-negative bacteria in a sample. Using standard methodology well known in the art, a diagnostic assay can be constructed by coating on a surface (i.e. a solid support) for example, a microtitration plate or a membrane (e.g. nitrocellulose membrane), all or a unique portion of the glycosylated pili described above, for example the O-antigen, and contacting it with the serum of a person suspected of having a Gram-negative bacterial infection. The presence of a resulting complex formed between glycosylated pili and antibodies specific therefor in the serum can be detected by any of the known methods common in the art, such as fluorescent antibody spectroscopy or colorimetry. This method of detection can be used, for example, for the diagnosis and typing of Gram-negative bacterial infections.

The adhesion properties of the Gram-negative bacteria are critical to its virulence and central to the development of pathology. Consequently, the ability of an individual to reduce bacterial adhesion would determine the patient's ability to prevent infection or disease. This may take the form of antibodies which inhibit the adhesion of pili to cells; this can be measured in an assay for the detection of glycosylated pili as described below. Such assays can be used to screen individuals after receiving a Gram-negative vaccine to measure the production of protective antibodies. Another mechanism to reduce adhesion of pili to cells is by down-regulating or altering the adhesion receptors present on the cells. Glycosylated pili can be used to measure the availability of cell receptors by contacting labeled glycosylated pili to target tissue either ex vivo or in vivo and measuring the degree to which labeled pili bind to target tissue. Pili can be labeled by any detectable label known in the art such as a radionuclide, for example. In addition, pili, glycosylated or unglycosylated can be used as receptor analogs to block the adhesion receptors present on host cells, thereby reducing or inhibiting the adhesion of bacteria to host cells. These pili can be administered in a mouthwash for example.

In yet another embodiment, the present invention relates to a method of detecting the presence of Gram-negative bacteria pili in a sample. Using standard methodology well known in the art, a diagnostic assay can be constructed by coating on a surface (i.e. a solid support) for example, a microtitration plate or a membrane (e.g. nitrocellulose membrane), antibodies specific for Gram-negative pili suspected, and contacting it with serum or tissue sample of a person suspected of having Gram-negative bacterial infection. The presence of a resulting complex formed between pili in the serum and antibodies specific therefor can be detected by any of the known methods common in the art, such as fluorescent antibody spectroscopy or colorimetry. This method of detection can be used, for example, for the diagnosis of Gram-negative bacterial infection or for typing the specific Gram-negative bacteria causing such an infection.

In another embodiment, the present invention relates to a diagnostic kit which contains glycosylated pili from a specific strain or species Gram-negative bacteria or several different strains and species of Gram-negative bacteria and ancillary reagents that are well known in the art and that are suitable for use in detecting the presence of antibodies to Gram-negative bacteria in serum or a tissue sample. Tissue samples contemplated can be monkey and human, or other mammals.

In yet a further embodiment, the present invention relates to DNA or nucleotide sequences for use in detecting the presence or absence of $P.$ $aeruginosa$ using the polymerase chain reaction (PCR). The DNA sequence of the present invention can be used to design primers which specifically bind to the pilO DNA for the purpose of detecting the presence, absence, or quantitating the amnount of $P.$ $earuginosa$. The primers can be any length ranging from 7–40 nucleotides, preferably 10–15 nucleotides, most preferably 18–25 nucleotides. Reagents and controls necessary for PCR reactions are well known in the art. The amplified products can then be analyzed for the presence or absence of pilO sequences, for example by gel fractionation, with or without hyridization, by radiochemistry, and immunochemical techniques. This method can also be used for typing a Gram-negative bacterial infection.

In yet another embodiment, the present invention relates to a diagnostic kit which contains PCR primers specific for pilO, and ancillary reagents that are well known in the art and that are suitable for use in detecting the presence or absence of $P.$ $aeruginosa$ in a sample using PCR. Samples contemplated can be human or other mammals.

In another embodiment, the present invention can be used to diagnose $P.$ $aeruginosa$ infection by using the DNA sequences for detecting the presence or absence of pilO in genomic DNA using hybridization assays such as Southern or northern hybridizations and other hybridization assays well known to a person with ordinary skill in the art.

In another embodiment, the present invention relates to a vaccine for protection against Gram-negative bacterial infections. The vaccine comprises glycosylated pili, or a portion thereof, from a specific strain or species of Gram-negative bacteria or preferably, a pool of glycosylated pili from different strain or species of Gram-negative bacteria to be used as a multivalent vaccine. The vaccine can be prepared by inducing expression of a recombinant expression vector comprising pilA and pilO in a Gram-negative host(s) and purifying the glycosylated pili described above. The purified solution is prepared for administration to mammals by methods known in the art, which can include filtering to sterilize the solution, diluting the solution, adding an adjuvant and stabilizing the solution. The vaccine can be lyophilized to produce a vaccine against Gram-negative bacteria in a dried form for ease in transportation and storage. Further, the vaccine may be prepared in the form of a mixed vaccine which contains the glycosylated pili described above and at least one other antigen as long as the added antigen does not interfere with the effectiveness of the vaccine and the side effects and adverse reactions are not increased additively or synergistically.

The vaccine may be stored in a sealed vial, ampule or the like. The present vaccine can generally be administered in the form of a liquid or suspension. In the case where the vaccine is in a dried form, the vaccine is dissolved or suspended in sterilized distilled water before administration. Generally, the vaccine may be administered orally, subcutaneously, intradermally or intramuscularly but preferably intranasally in a dose effective for the production of neutralizing antibody and protection from infection or disease.

In another embodiment, the present invention relates to a method of reducing Gram-negative bacterial infection symptoms in a patient by administering to said patient an effective amount of anti-pili or anti-glycosylated pili antibodies, or pili (glycosylated or unglycosylated) as described above, or other agents capable of blocking pili function. Since glycosylated pili are involved in adhesion of bacteria to host cells, inhibiting or reversing the adhesion of bacteria may reduce or eliminate the development of Gram-negative bacterial infections. When providing a patient with anti-pili or anti-glycosylated pill antibodies, or agents capable of inhibiting pili function or expression for example receptor analogs such as pili themselves to a recipient patient, the dosage of administered agent will vary depending upon such factors as the patient's age, weight, height, sex, general medical condition, previous medical history, etc. In general, it is desirable to provide the recipient with a dosage of the above compounds which is in the range of from about 1 pg/kg to 10 mg/kg (body weight of patient), although a lower or higher dosage may be administered.

In another embodiment, the present invention provides a method for large scale production of pili. Pure, undenatured pili in milligram quantities are required for vaccine use. Current methods of pili purification present difficulties. Cells grown on solid media adhere tenaciously, producing large quantities of slime. The vigorous treatment required to dislodge the cells damages the pilus fibers and releases cellular materials (LPS is a common contaminate; flagella, which copurify with the pili are usually present). Growth in broth cultures, especially using high levels of agitation, suppresses production of pili, probably because they are broken off during this vigorous agitation.

The present method overcomes the suppression of pili production in broth cultures by using RpoN⁻ strains for pili production. Any Gram-negative bacterial strain can be made RpoN⁻ according the published protocols (Ishimoto and Lory, 1989, *Proc. Natl. Acad. Sci. USA* 86: 1954–1957). This new method routinely yields milligram quantities of pure native pili per liter of culture by overcoming the suppression of pili production in broth and comprises the steps of:

(1) transforming an RpoN⁻ Gram-negative bacteria with a vector containing the pilin structural gene with or without pilO;

(ii) growing the transformed bacteria in broth culture with vigorous agitation; and (iii) purifying pili from the supernatant fluid of said broth cultures.

In yet another embodiment, the present invention provides immunogenic epitopes from the pilA structural pilin gene representing possible glycosylation recognition sequences. These epitopes were mapped by standard peptide mapping techniques. These epitopes include the amino acid sequences designated SEQ ID NO:3 and SEQ ID NO:4. These peptides can be generated in any manner, including for example, chemical synthesis, or expression of a recombinant expression system. In addition the polypeptide can be fused to other proteins or polypeptides which increase its antigenicity, such as adjuvants for example, thereby producing higher titers of anti-pilin antibodies for protection against *P. aeruginosa* infection. In addition, these peptides may be used with or without glycosylation as a vaccine or for the production of antibodies which can then be used to generate passive immunity against *P. aeruginosa* infection.

In addition, the strain 1244 peptide sequence conferring glycosylation can be incorporated into other *P. aeruginosa* cell surface proteins of potential vaccine value using standard recombinant DNA methodologies. Examples of such cell surface proteins include flagella and outer membrane proteins such as F and P. This recognition sequence could be likewise incorporated into surface proteins of vaccine potential from other bacteria such as Bordetella pelussis, Francisella species, Neisseria meningiditis, Neisseria gonorrhoeae, Vibrio cholerae, Brucella species, certain strains of *Escherichia coli*, and Yersinia species. Expression of pilO from a plasmid in such an organism would result in the addition of the organisms specific O-antigen to this protein.

Described below are examples of the present invention which are provided only for illustrative purposes, and not to limit the scope of the present invention. In light of the present disclosure, numerous embodiments within the scope of the claims will be apparent to those of ordinary skill in the art.

The following MATERIALS AND METHODS were used in the examples that follow.

Bacterial strains and culture conditions. *P. aeruginosa* 1244, a clinical isolate which has been used in pilus-mediated adhesion studies (Ramphal et al., 1984, *Infect. Immun*. 44: 38–40), was provided by A. T. McManus, U.S. Army Institute of Surgical Research, San Antonio, Tex. *P. aeruginosa* strain 1244N3, a mutant which is unable to make pili or produce pilin (Ramphal et. al., 1991, *Infect. Immun*. 59: 1307–1311) due to an inactivated rpoN gene, was furnished by S. Lory, University of Washington. Cultures were grown on LB medium (Sambrook etal., 1989, *Molecular Cloning: a Laboratory Manual*, vol. 1, 2nd edn. Cold Spring Harbor, N.Y.: Cold Spring Harbor Laboratory) at 37° C. Antibiotic concentrations in selective media used for *P. aeruginosa* were as follows: carbenicillin (Cb), 500 µg ml⁻¹; tetracycline (Tc), 50 µg ml⁻¹. Antibiotics used with *E. coli* were: ampicillin (Ap), 75 µg ml⁻¹; spectinomycin (Sp), 25 µg ml⁻¹; tetracycline (Tc), 10 µg ml⁻¹.

Nucleotide sequencing. The Sanger dideoxy method (Sanger et al., 1977, *Proc. Natl. Acad. Sci. USA* 74: 5463–5467) was used. The template was single-stranded M13 subclones of phage Lambda or plasmid clones (Castric et al., 1989, *Mol. & Gen. Genet*. 216: 75–80) containing DNA downstream from the pilA gene. Synthetic primers, derived from known sequences, or universal primers were employed.

Plasmid constructs. The plasmid pPAC46, which contained both pilA and pilO, was constructed by ligating the SphI-HindIII plasmid fragment containing the pilA and adjacent DNA (FIG. 2) of pPAC202 (Castric et al., 1989, supra) to plasmid pUC18 digested with these same enzymes. The EcoRI-HindIII fragment of this construct, pPAC 124, was ligated with the broad host range expression vector pMMB66EH (Ap', lacI^q; Furste et al., 1986, supra) which had been digested with the same restriction enzymes. Plasmid pPAC24, which contained pilA, but not pilO, was constructed by ligating the pPAC124 EcoRI-NheI fragment containing thepilA gene with pUC19 digested with EcoRI and XbaI. The EcoRI-HindIII fragment of this construct, which contained only the pilA gene, was ligated with pMMB66EH digested with the same restriction enzymes. The pilA gene of both pPAC24 and pPAC46 was under control of the vector tac promoter. Since the SphI site used in plasmid construction is located within the pilA promoter neither pPAC24 nor pPAC46 were able to express the pilin structural gene using the *P. aeruginosa* promoter. Plasmid DNA was introduced into *E. coli* by transformation (Sambrook et al., 1989, supra), and was transferred to *P. aeruginosa* by triparental mating (Ruvkun & Ausubel, 1981, *Nature* 289: 65–88).

Northern blot analysis. RNA was extracted as described by Reddy (1989, In *Current Protocols in Molecular Biology*, vol. 1, 4.4.1.–4.4.7. Edited by F. M. Ausubel et al. New York: John Wiley) and separated by formaldehyde-agarose gel electrophoresis, stained with ethidium bromide, and transferred to nitrocellulose paper by capillary blot as described by Sambrook et al., (1989, supra). Probe DNA, isolated from pPAC24 or pPAC46, was labelled by nick translation using [α-$^{32}$P] dCTP. Prehybridization, hybridization, and washing steps were as described by Sambrook et al., 1989. Detection of hybridization was by autoradiography. Densitometric scanning was carried out using an LKB Ultroscan laser densitometer.

Purification of pili. Production of pili by expression of the pilA genes of plasmids pPAC24 and pPAC46 in *P. aeruginosa* 1244N3 was carried out using LB agar- or LB broth-cultures grown in the presence of 5 mM isopropyl-thiogalactoside (IPTG). LB agar-grown cells were resuspended in LB broth. These cells (as well as broth-grown cells) were depiliated by four excursions through a 22-gauge needle. Cells were removed by centrifugation (7,500 g for 15 min). The pili remaining in the supernatant fluid were purified by a variation of the method of Silipigni-Fusco (1987, *Studies in the role of somatic pili as virulence and inmunityfactors in the pathogenicity of Pseudomonas aeruginosa*. Ph.D. thesis, University of Pittsburgh, USA). In this procedure the supernatant fluid was made 0.1 M with respect to MgCl$_2$, and stored on ice for 60 min. The resulting precipitate, which contained the pilus fibres, was removed by centrifugation at 12,000 g for 15 min.

Pilin analysis. N-terminal amino acid sequence analysis and amino acid analysis was performed on purified pilin from strain 1244N3(pPAC24). This protein was subjected to PAGE (15% T) which was followed by electroblotting to polyvinylidene difluoride paper. Preliminary staining showed that pilin was the major protein present and that it was well separated from the minor contaminants present. Pilin bands were excised and subjected to gas-phase sequencing and to amino acid analysis (University of Pittsburgh Peptide Facility).

Pilin immunoblot analysis. Pilins were separated by PAGE (12.5% T in the presence of either 0.1% SDS at 5° C. or 30.0 mM octyl glucoside at 15° C.) or subjected to isoelectric focusing (pH 3.0 to 9.5) in the presence of 30.0 mM octyl glucoside at 15° C. using the LKB-Pharmacia Phastsystem. Proteins were transferred to nitrocellulose paper by diffusion blotting; pilin adsorbed to the paper was detected using anti-pilin monoclonal antibody 6–45 (Saiman et al., 1989, Immun. 57: 2764–2770) as previously described (Castric et al., 1989, supra). The presence of pilin-bound sugar residues was detected by first derivatizing purified pili using the DIG Glycan Detection kit of Boehringer Mannheim Biochemica (Indianapolis). This protein was subjected to SDS-PAGE (12.5% T) using the BioRad MiniProtean II system in which temperature was neither controlled nor monitored. Pilin was electroblotted to nitrocellulose paper, probed with an alkaline phosphatase-labelled antibody specific for the hapten used in pilin derivatization, and developed as described by Boehringer Mannheim Biochemica (Indianapolis).

Electron microscopy. Cells to be analyzed by electron microscopy were grown on LB agar plates at 37° C. for approximately eighteen hours and suspended in phosphate buffered saline. The cells were coated on 200 mesh formvar-coated copper grids, subjected to staining with 1% uranyl acetate, and viewed in a Philips 201 electron microscope.

Pill functionality tests. The phage sensitivity test was performed by streaking a loop of pilus-specific phage PE69 on an LB agar plate. This was cross-streaked with diluted *P. aeruginosa* 1244 strains to be tested. Phage sensitivity was interpreted from the absence of growth at the cross-streak junction. Twitching (Henrichsen, 1983, *Annu. Rev. Microbiol.* 37: 81–93) was determined by streaking strains of interest on a well dried LB agar plate where motility was scored as spreading growth at between 48 and 72 hours at 37° C.

EXAMPLE 1

Nucleotide Sequence Analysis

The nucleotide sequence downstream from the *P. aeruginosa* strain 1244 pilA gene contains a potential transcriptional termination structure situated between positions 626 to 708 (noted previously in Castric et al., 1989, supra). A ribosome-binding site (GGAG) is seen at position 717 followed closely by three start codons, the first of which is located immediately in frame with a stop codon (TGA). The second and third, GTG and ATG, are in frame with each other and begin an open reading frame (referred to hereafter as pilO) which extends 1383 base pairs, using the ATG codon, to position 2114. Codon usage of the 461 codons of the pilO gene is consistent with that of most other *P. aeruginosa* genes (West & Iglewski, 1988, *Nucleic Acids Res.* 16: 9323–9335). However, significant differences are seen when it is compared, with the adjacent pilA gene or with the pilA genes of other *P. aeruginosa* strains (West & Iglewski, 1988, supra; Castric & Deal, 1994, supra). While the phe codons, TTT and TTC, have frequencies of 20/29 and 9/29, respectively, in the pilA gene, these codons occur at rates of 6/25 and 19/25, respectively, in the pilO gene. The arg codons, CGT and GCG, appear at rates of 26/31 and 2/31 in the pilA gene, but occur at rates of 7/31 and 11/31, respectively, in the pilO gene. In addition, the G+C % content of pilO (60.1%) is consistent with the general range given for *P. aeruginosa* chromosomal DNA (West & Iglewski, 1988), but quite different from the value of 52.2% determined for the strain 1244pilA gene. A search of the Genbank database revealed no sequences with significant homology to the pilO gene.

A tRNA$^{thr}$ gene, which contains an anticodon recognizing the rare codon ACG, can be seen just downstream of the pilO gene between positions 2166 and 2241, and is followed, between positions 2245 and 2282, by a potentially bidirectional transcriptional stop containing a 17 bp loop stem. A tRNA gene and transcriptional stop region have been noted previously (Hobbs et al., 1988, Gene 62: 219–227) as occurring immediately downstream from the *P. aeruginosa* strain PAK pilA gene, and may also be seen in the analogous region of the pilA genes of *P. aeruginosa* strains PAO and PA 103 (Johnson et al., 1986, supra). A homology comparison (FIG. 1) shows that the tRNA-transcriptional stop region described in this paper is virtually identical with the pilA-proximal regions of strain PA 103 beginning at position 2421 and continuing 275 base pairs to the end of the sequence. It is interesting to note that the first S bases of this region (GAGTG) are also found, as a direct repeat, in the pilA-O intragenic region gene beginning at position 676, suggesting a possible site of genetic recombination. These results are summarized in FIG. 2 where the organization of these regions may be compared.

EXAMPLE 2

Transcription of PilO

Figure 3A:
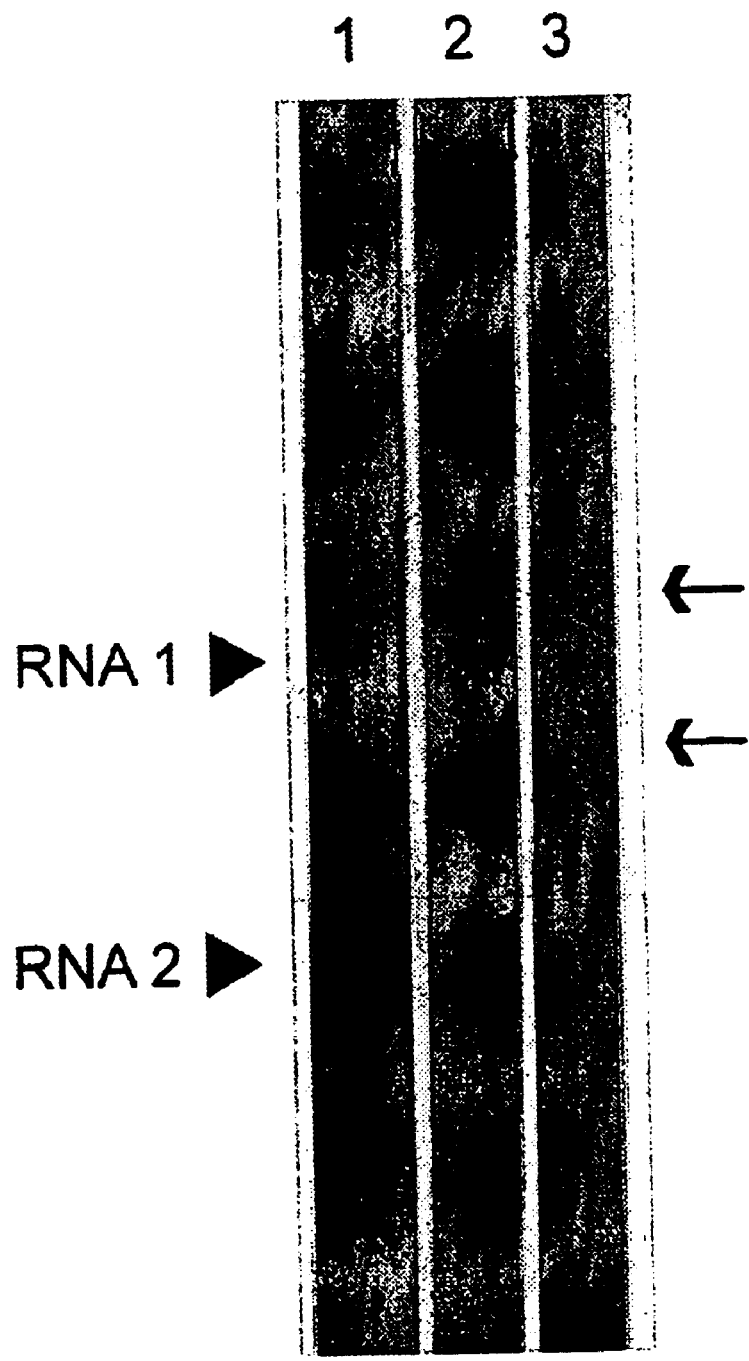
FIG. 3A & B are Northern blot analysis of mRNA extracted from P. aeruginosa strain 1244. 3A. Probes were prepared from restriction fragments of cloned DNA indicated in the FIG. 2 map as follows: Lane 1, Probe 1 (the SphI-NheI fragment); Lane 2, Probe 2 (the NheI-PstI fragment); Lane 3, Probe 3 (the PstI-HindIII fragment). Arrows indicate positions of E. coli strain HB 101 ribosomal RNA. 3B. Densitometric scan of lane 1 of panel A of this figure. Scanning was from bottom to top of the autoradiogram shown. Electrophoresis point of origin is marked by the arrow.
Figure 3B:
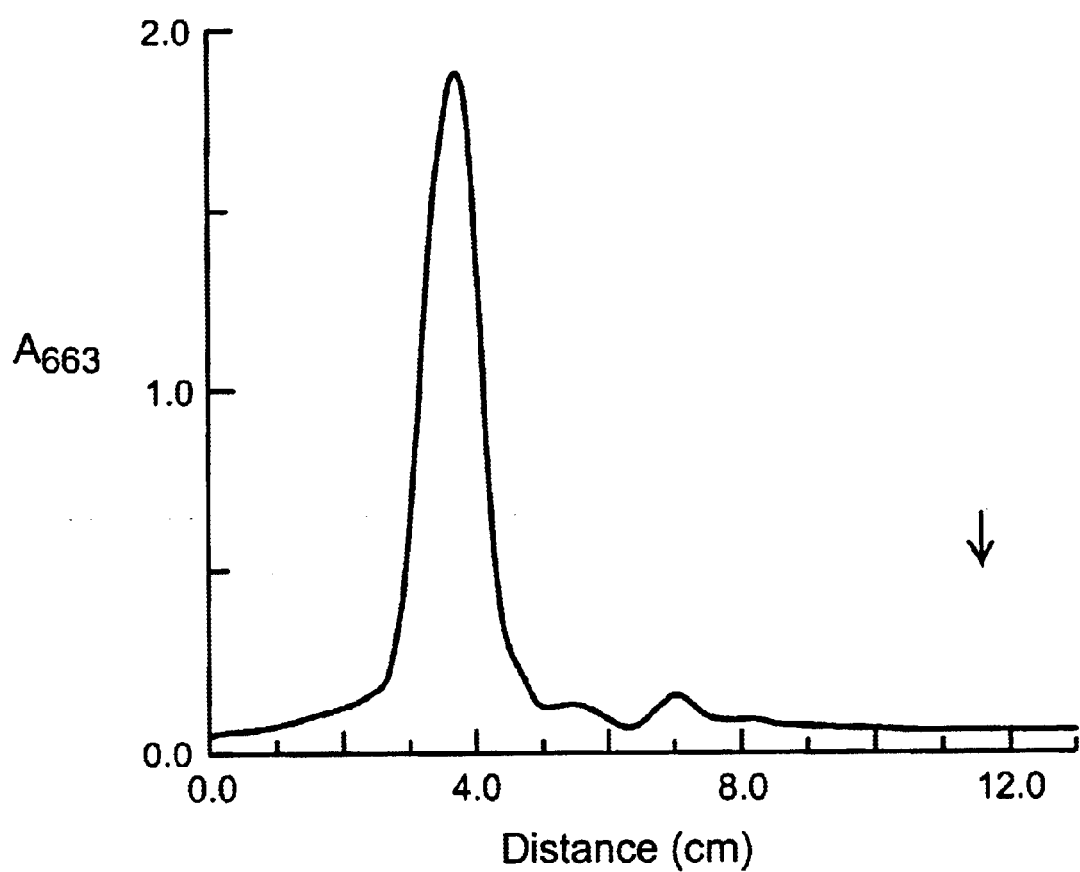

Northern blots (FIG. 3) of strain 1244 mRNA showed that probe 1, composed of pilA DNA, recognized 650 base (RNA 2) and 2200 base (RNA 1) species. The smaller transcript was present in approximately a 100-fold excess over the larger mRNA as determined by densitometric scanning. By analogy with work on other *P. aeruginosa* pilA genes (Johnson et al., 1986) the transcription startpoint may be presumed to begin between positions 150 and 160, suggesting that the larger transcript extends into the pilO region.

The intermediate-sized RNA fragments might be formed by early termination, due to the loop structure referred to earlier, or might be degradation products of the larger species. Probe 2, which was composed of pilO DNA, hybridized only with the larger fragment and the intermediate pieces suggesting that the origin of the 2200 base mRNA is in the pilA region and that synthesis of this molecule extends downstream through the pilO gene. This was confirmed by the reaction of probe 3 which was composed of DNA from the latter part of the pilO gene and the tRNA-transcriptional stop region. This probe hybridized with the larger fragment but with neither thepilA transcript nor the intermediate fragments. This probe also hybridized with a very small RNA population, presumably tRNA produced by the pilO-associated gene as well as with cross-reacting species. Overall these results indicate that pilA, pilO and probably the adjacent tRNA gene are part of a single transcriptional unit which utilizes the pilA promoter.

EXAMPLE 3

Influence of PilO on Pilus Function

Since both pilA and pilO are part of the same transcriptional unit, the inactivation of the pilA promoter will also eliminate pilO expression. *P. aeruginosa* strain 1244N3 is a mutant which is unable to make pili or produce pilin (Ramphal et al., 1991, *Infect. Immun.* 59: 1307–1311) due to an inactivated rpoN gene. This strain was used as the genetic background for expression of the pilA gene, carried on recombinant plasmids pPAC24 (containing only pilA) or pPAC46 (bearing both pilA and pilO), under control of a tac promoter. Electron microscopy showed that while strain 1244N3 produced no pili both derivatives 1244N3(pPAC24) and 1244N3(pPAC46), when grown in the presence of IPTG, produced pilus fibres which were indistinguishable from those of the wild-type (results not shown). Both strains 1244N3(pPAC24) and 1244N3(pPAC46), in the presence of IPTG, were sensitive to the pilus-specific bacteriophage PE69 and demonstrated twitching motility on dried agar plates, properties lacking in strain 1244N3. These results indicated that the absence of pilO did not appear to influence the ability of the pilus to extend and retract, qualities necessary for twitching and for phage sensitivity.

EXAMPLE 4

Influence of PilO on Pilin Structure

Figure 4A:
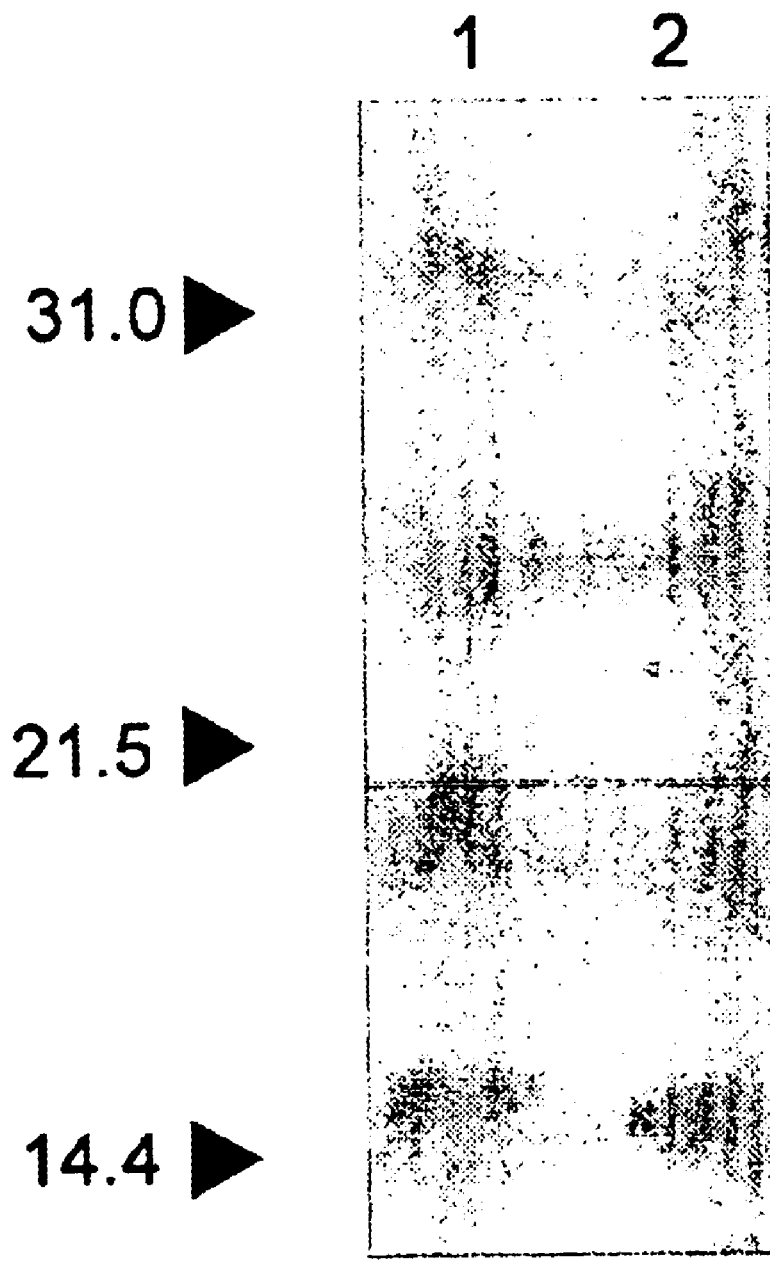
FIG. 4A & B show immunodetection of electrophoretically separated P. aeruginosa pilin. 4A. SDS-PAGE of pilin at 5° C. Lane 1, 3 μg pilin produced by P. aeruginosa strain 1244N3(pPAC46), Lane 2, 3 μg pilin produced by P. aeruginosa strain 1244N3(pPAC24). Molecular weights are given as times $10^{-3}$. 4B. Isoelectric focusing of pilin at 15° C. Lane 1, 3 μg pilin produced by P. aeruginosa strain 1244N3 (pPAC24), Lane 2, 3 μg pilin produced by P. aeruginosa strain 1244N3(pPAC46). The pH gradient was determined by focusing pI standards on an identical gel in the absence of octyl glucoside.
Figure 5:
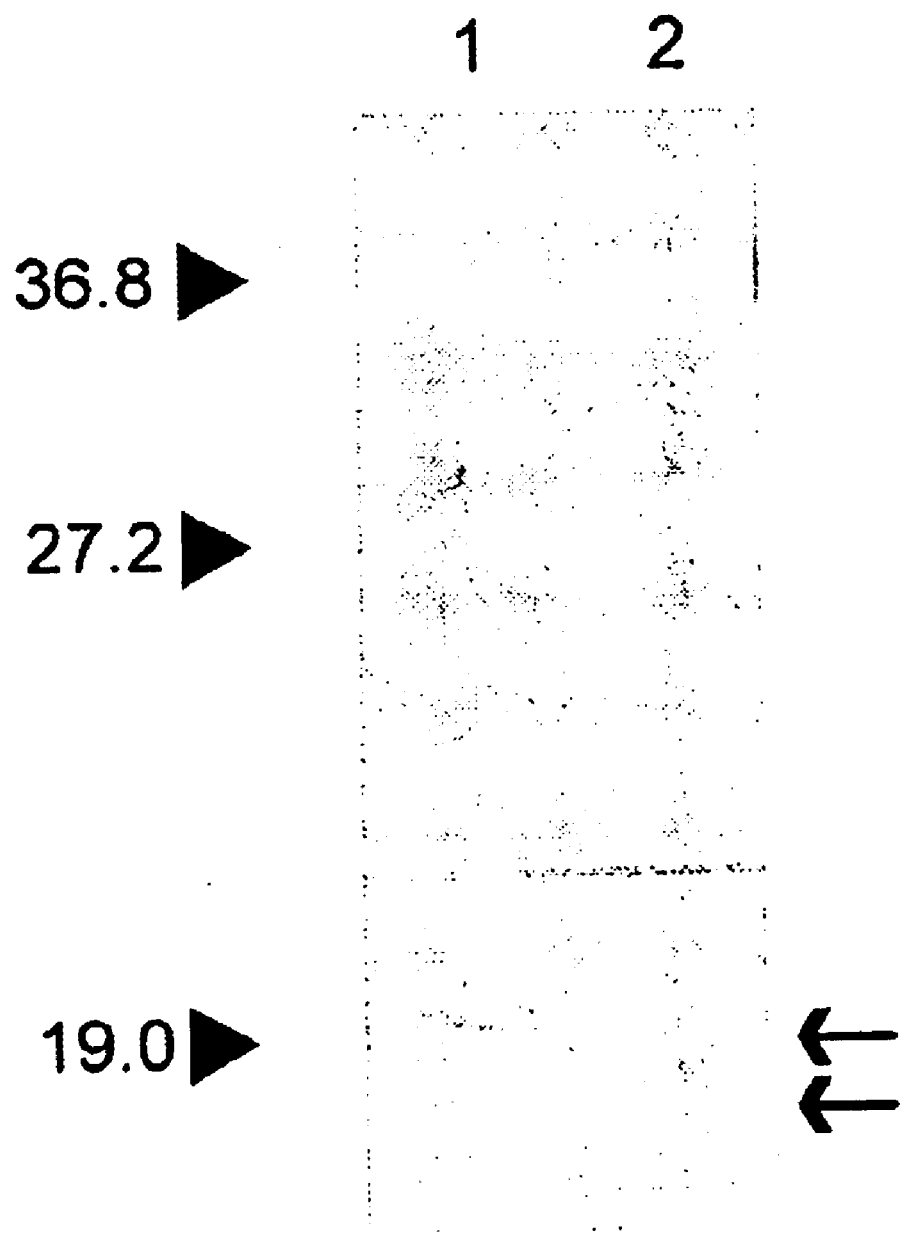
FIG. 5 shows the detection of P. aeruginosa pilin carbohydrate by immunoblot. Lane 1, 10 μg pilin produced by P. aeruginosa strain 1244N3(pPAC46), Lane 2, 10 μg pilin produced by P. aeruginosa strain 1244N3(pPAC24). Molecular weights are given as times $10^{-3}$. Arrows indicate positions of these pilins on an identical blot using monoclonal antibody 6–45 for detection.

Although strain 1244N3 was unable to produce pilin, as determined by Western blot (results not shown), complementation of this strain with either plasmid pPAC24 or pPAC46, under inducing conditions, allowed production of this protein (FIG. 4A). While the molecular weight of mature pilin of strain 1244 predicted from the nucleotide sequence of the pilA gene (Castric el al., 1989, supra) is 15,653, the apparent size of pilin produced by strain 1244N3 (pPAC46), or by wild-type strain 1244 (results not shown) is approximately 16,900. Pilin produced by strain 1244N3 (pPAC24), which lacks a functional pilO gene, had an apparent molecular weight of 15,600. Identical results were obtained when gradient SDS-PAGE was employed. A small fraction of the pilin produced by strain 1244N3(pPAC24) migrated with wild-type pilin when the BioRad MiniProtean II PAGE system (15% T) was employed (results not shown).

To explore the significance of this apparent molecular weight difference it was necessary to see if the N-terminus of pilin produced by strain 1244N3(pPAC24) was in any way altered. When this protein was subjected to N-terminal amino acid analysis, the sequence of mature pilin, XTLIELM (the first residue produced no reaction presumably because it was the masked amino acid N-methylphenylalanine), was obtained. Amino acid analysis of blotted pilin was also carried out to determine the integrity of the carboxy-terminal region. The pilin of *P. aeruginosa* 1244 contains 6 prolines (Castric et al., 1989), mainly in the carboxy-terminal region. The observed molecular weight difference of approximately 1,200, if caused by cleavage in this region, would require breaking the bond between residues 136 and 137 of mature pilin resulting in a change in apparent proline number from 6 to 3. Normalization (with alanine) of actual values obtained gave a proline/alanine (P/A) ratio of 0.36, with a P/A ratio of 0.20 predicted for a truncated form and a P/A ratio of 0.35 predicted for mature pilin. Normalization with leucine values gave a proline/leucine (P/L) of 0.68 (a P/L ratio of 0.33 is predicted for a truncated form and a P/L ratio of 0.67 for mature pilin). These results suggest that the pilin carboxy-terminal region must be substantially intact.

Purified pili from strains 1244N3(pPAC24) and 1244N3 (pPAC46) were treated with periodic acid to oxidize any sugar residues present. These proteins were then treated with digoxygenin-succinyl-ε-amidocaproic acid hydrazide which will form a covalent bond with oxidized sugars. After SDS-PAGE these proteins were electroblotted to nitrocellulose paper and probed with an anti-digoxygenin antibody preparation. FIG. 4 shows that pilin from strain 1244N3 (pPAC46) reacted with this antibody indicating the presence of sugar moieties, while pilin from strain 1244N3(pPAC24) gave no reaction.

Pili were dissociated into pilin monomers and dimers in the presence of 30.0 mM octyl glucoside (Watts et al., 1982a, *Can. J. Biochem.* 60: 867–872; Watts et al., 1982b, *J. Bacteriol.* 151: 1508–1513; Watts et al., 1983, *Biochemistry* 22: 687–691), subjected to isoelectric focusing, then blotted to nitrocellulose paper, and probed with pilin-specific monoclonal antibodies. Pilin produced by strain 1244N3(pPAC46) or by wild-type strain 1244 (results not shown) had a pI of 4.75 (FIG. 4B). Pilin from strain 1244N3(pPAC24), which lacked a functional pilO gene, had a pI of approximately 6.25. The pI of mature strain 1244 pilin is predicted from the pilA gene sequence (assuming that the amino-terminus is blocked and the two cysteines form a disulfide) to be 7.00. These results indicate that a significant alteration in pilin charge arrangement (neutralization of positive charges or introduction of negative ones) is brought about by the presence of the pilO gene. The difference in charge between these two pilin forms was confirmed by PAGE in the presence of 30.0 mM octyl glucoside at pH 8.8. Pilin from strain 1244 or strain 1244N3 (pPAC46) had a greater net negative charge than pilin from strain 1244N3(pPAC24) (results not shown). Pilin from strains 1244 and 1244N3(pPAC46) also focused at pH 4.75 in the presence of 8.0 M urea and 2.5% (v/v) Triton X-100 (results not shown). Pilin preparations from strain 1244N3 (pPAC46) or the wild-type strain contained trace amounts of the neutral pilin form (results not shown) possibly due to chemical or enzymatic action. The small: amounts of the acidic pilin form produced by strain 1244N3(pPAC24) (FIG. 4B), as well as the higher molecular weight form described above, may be due to low levels of pilO gene expression by the host strain. These results altogether suggest that the *P. aeruginosa* strain 1244pilO gene is required for a posttranslational pilin modification, specifically a glycosylation.

EXAMPLE 5

Preparation of Glycosylated PA1244 Pili

One liter (in a 2.8 liter Fernbach flask) of a medium (LB broth containing Carbenicillin [200 μg/ml], Tetracyline [50

μg/ml], and isopropyl thiogalactoside [IPTG, 5 mM]) was inoculated with 25 ml of an overnight culture of *Pseudononas aeruginosa* 1244N3(pPAC46) grown with the same medium (minus the IPTG). This host strain is RpoN⁻. The inoculated medium was incubated at 37C with rotary agitation 250 rpm for 7 hours. The overnight starter culture was grown under the same conditions in a 125 ml Erlenmyer flask.

After incubation the cells were removed by centrifugation (4,200×g for 15 min). 30 g of Polyethylene glycol (PEG) 6000 and 20.3 g $MgCl_2$ were added to the supernatant fluid which was stored overnight at 4C. The light grey-tan precipitate (containing the pili) was removed by centrifugation (13,20×g for 30 min).

This material was suspended with 50 ml 10.0 mM Tris/HCl, pH 7.6 containing 20% sucrose and centrifuged (4,200×g for 15 min). The precipitate was discarded and the supernatant fluid was reprecipitated with PEG and $MgCl_2$ as described above, and stored overnight at 4C. The light grey-tan precipitate (containing the pili) was removed by centrifugation (13,20×g for 30 min) and suspended with 25 ml 10.0 mM Tris/HCl, pH 7.6 containing 20% sucrose.

Ammonium sulfate was added to 35% saturation. After 30 min at 4C this material was centrifuged (4,200×g for 15 min) and the precipitate discarded. Ammonium sulfate was added to the supernatant fluid to 65% saturation. After 60 min at 4C this material was centrifuged (4,200×g for 15 min) and the supernatant fluid was discarded. The pellet contained the pili were subjected to polyacrylamide gel electrophoresis (PAGE) which showed, with silver staining, only trace amounts of contaminating protein and only minor amounts of LPS on gels in which pilin was overloaded. This procedure routinely produced 10 to 20 mg of pilin protein (as determined by the BCA test) per liter of cells.

EXAMPLE 6

Animal Model

ICR mice (25–30 g) were immunized with *P. aeruginosa* strain 1244 pili at a concentration of 5 mg/mouse/dose diluted in physiologic saline. The following immunization schedules were used to determine antibody response: i.n./i.n., s.c./s.c., i.p./i.p., i.n./s.c., s.c./i.n., i.n./i.p., i.p./i.n.. The time interval between the doses was 7 days. For i.n. immunization, mice were anesthetized i.p. with ketamine HCl (80 mg/kg) and xylazine HCl (8 mg/kg) prior to the instillation of pili. Pili were delivered i.n. in a final volume of 25 μl using sterile aerosol resistant pipet tips for each mouse to prevent contamination. The final volume for i.p. and s.c. injection was 100 μl. Control mice received physiologic saline only At days +3, +7, +10 and +14 after the second dose, mice were sacrificed by $CO_2$ inhalation to obtain serum samples via cardiac puncture as well as bronchoalveolar lavage (BAL) samples for antibody titers. For BAL samples, lungs were washed once with 1 ml of sterile physiologic saline via a 25 G hypodermic needle inserted into the trachea.

Antibody titers were determined by means of an ELISA using 96-well plates coated with *P. aeruginosa* 1244 pili at a concentration of 2 mg/ml (50 ml/well, 4° C., over night [O/N]). After blocking and washing, samples were serially diluted (2-fold) in duplicate in blocking buffer and incubated O/N at 4° C. Bound antibodies were detected using goat-anti-mouse-IgG/alkaline phosphatase labelled, goat-anti-mouse-IgM/alkaline phosphatase labelled, and goat-anti-mouse-IgA/alkaline phosphatase labelled (Incubation O/N, 4° C.); plates were developed with p-Nitrophenylphosphate in diethanolamine buffer and read in a Biotek® Ceres 900 C ELISA reader. ELISA titers are defined as $log_{10}$ of the dilution which gave a change of $A_{405}$ of 0.200 after 30 min.

For protection studies, *P. aeruginosa* 1244 was grown to mid-log phase in trypticase soy broth for 4 h at 37° C. After washing the bacteria with physiologic saline, the $OD_{650}$ was adjusted to 0.480 which corresponded to an estimated CFU count of $2\times10^8$/ml. Mice were challenged i.n. using 2 different doses ($LD_{100}$, $LD_5$) at day +7 after the second dose of pili. Anesthesia was done as described above, and bacteria were delivered in a final volume of 50 ml. Mortality and body weight were monitored daily for 14 days. Control mice received physiologic saline only. Time to recovery in sublethal challenge experiments was defined as number of days until the baseline body weight was regained or (if animals did not reach their baseline body weight) as number of days until stabilization of body weight (3 consecutive days with weight change 0.5 g).

TABLE 1

ANTIBODIES AGAINST PILI (Mice: ICR)

| | BAL | | | | Serum | | | |
|---|---|---|---|---|---|---|---|---|
| Route, | | | | Sample day: | | | | |
| Ig class | 3 | 7 | 10 | 14 | 3 | 7 | 10 | 14 |
| IN/IN | | | | | | | | |
| IgG | 2.76 | 2.80 | 2.15 | 1.83 | 4.13 | 5.59 | 4.09 | 5.12 |
| IgM | 1.85 | 0.50 | 0.50 | 0.50 | 3.91 | 2.97 | 2.93 | 2.80 |
| IgA | 1.90 | 2.74 | 2.00 | 0.50 | 2.50 | 2.40 | 2.09 | 0.50 |
| IN/SC | | | | | | | | |
| IgG | 0.50 | 1.85 | 1.77 | 1.70 | 3.64 | 5.61 | 5.78 | 5.61 |
| IgM | 0.50 | 0.50 | 0.50 | 0.50 | 3.44 | 3.95 | 3.64 | 2.85 |
| IgA | 0.50 | 0.50 | 0.50 | 0.50 | 1.15 | 1.40 | 1.27 | 0.50 |

TABLE 2

ANTIBODIES AGAINST LPS (Mice: ICR)

| | BAL | | | | Serum | | | |
|---|---|---|---|---|---|---|---|---|
| Route, | | | | Sample day: | | | | |
| Ig class | 3 | 7 | 10 | 14 | 3 | 7 | 10 | 14 |
| IN/IN | | | | | | | | |
| IgG | 0.50 | 0.50 | 0.50 | 0.50 | 2.05 | 1.90 | 1.77 | 2.37 |
| IgM | 0.50 | 0.50 | 0.50 | 0.50 | 2.68 | 2.43 | 1.96 | 1.97 |
| IgA | 0.50 | 0.96 | 0.50 | 0.50 | 0.50 | 0.50 | 0.50 | 0.50 |
| IN/SC | | | | | | | | |
| IgG | 0.50 | 0.50 | 0.50 | 0.50 | 2.22 | 2.43 | 2.13 | 2.09 |
| IgM | 0.50 | 0.50 | 0.50 | 0.50 | 2.79 | 2.90 | 2.83 | 2.69 |
| IgA | 0.50 | 0.50 | 0.50 | 0.50 | 0.50 | 0.50 | 0.50 | 0.50 |

TABLE 3

ANTIBODIES AGAINST PILI (Mice: C3H/HeJ)

| Route | BAL | | | Serum | | |
|---|---|---|---|---|---|---|
| Ig class | IgG | IgM | IgA | IgG | IgM | IgA |
| IN/IN | 0.50 | 0.50 | 0.50 | 3.26 | 3.11 | 0.50 |
| IN/SC | 0.50 | 0.50 | 0.50 | 3.33 | 3.35 | 0.50 |

TABLE 4

ANTIBOTIES AGAINST LPS (Mice: C3H/HeJ)

| Route | BAL | | | Serum | | |
|---|---|---|---|---|---|---|
| Ig class | IgG | IgM | IgA | IgG | IgM | IgA |
| IN/IN | 0.50 | 0.50 | 0.50 | 1.49 | 2.09 | 0.50 |
| IN/SC | 0.50 | 0.50 | 0.50 | 1.39 | 1.86 | 0.50 | notes:
All data are medians (not means) from 3 mice. They represent the $\log_{10}$ of 10-fold dilutions which gave a change of $A_{410}$ of 0.200/15 min. Background readings (everything except serum or BAL samples) were always below 0.020. Serum samples from normal ICR as well as C3H/HeJ mice gave no readings higher than the background.
Data from C3H/HeJ mice are from day +7 after the 2nd dose only.
Limit of detection: 0.499 1:3

Every immunization schedule tested resulted in IgG and IgM antibody titers in serum as well as in BAL fluid. Only immunization twice via the i.n. route, however, yielded significant levels of IgA antibodies both locally and systemically. Based on these findings, we chose to compare wot different routes (i.n./i.n., i.n./s.q.) with the bacterial challenge given at day +7 after the boost dose. While all of the control mice died within 3 days, 66.7% of the mice immunized i.n./s.c. (P=0.03 1). In sublethal infections, time to recovery as measured by regaining body weight was shorter in the group immunized i.n./i.n. (7.1±0.8 days, mean ±SEM) than in the control group (9.6±0.8 days). Thus, we were able to demonstrate that pili from P. aeruginosa are highly immunogenic. Mucosal immunization via the intranasal route protects mice significantly from a lethal pulmonary challenge with the homologous strain and leads to faster recovery in sublethal lung infections.

EXAMPLE 7

Location of the Site of Pilin Glycosylation

Digestion of pure glycosylated strain 1244 pilin (apparent molecular weight as determined by SDS-PAGE was 16,800) with V8 protease produced a 9,000 molecular weight peptide which reacted with anti-LPS monoclonal 11.14 on Western blot. N-terminal analysis of this fragment showed that this peptide with this N-terminus would be predicted to have a molecular weight of 7,700. Altogether, these results show that the pilin glycosylation site is in the region bounded by residue 75 and the carboxy-terminus, encompassing peptide regions 3 (SEQ ID NO: 3) and 4 (SEQ ID NO:4), two regions found to contain linear B-cell epitopes (Castric and Deal, 1994, supra) and may be important in peptide vaccine design. Further, peptide sequencing indicated that residue 95 did not produce the expected threonine residue suggesting that epitope region 3 is the site of glycosylation.

Discussion

While glycosylation of prokaryotic proteins appears to be primarily restricted to the archaebacteria (Lechner & Wieland, 1989, *Annu. Rev. Biochem.* 58: 173–194), reports have suggested the association of polysaccharide with pili (Armstrong et al., 1981, *J. Bacteriol.* 145: 1167–1176; Robertson et al., 1977, *J. Gen. Microbiol.* 102: 169–177).

TABLE 5

| | | | | Survival (L/D) | | | | | | | Survival @ end of study | | |
|---|---|---|---|---|---|---|---|---|---|---|---|---|---|
| | Treat- | Challenge with | | day | | | | | | | | alive/ | % |
| Group # | ment | Strain | CFU given[a] | 0 | 1 | 2 | 3 | 4 | 5–13 | 14 | | total | alive |
| 10-6 | i.n.-i.n. | P. aer. | $6.1 \times 10^6$ | 5/0 | 5/0 | 5/0 | 3/2 | 3/0 | 3/0 | 3/0 | | 3/5 | 60 |
| 1-17 | " | 12.4.4 | $2.25 \times 10^6$ | 5/0 | 4/1 | 4/0 | 4/0 | 4/0 | 4/0 | 4/0 | | 4/5 | 80 |
| 1-20 | " | " | $6.75 \times 10^6$ | 5/0 | 5/0 | 4/1 | 4/0 | 3/1 | 3/0 | 3/0 | | 3/5 | 60 |
| total | " | " | $5.03 \times 10^6$ | 15/0 | 14/1 | 13/1 | 11/2 | 10/1 | 10/0 | 10/0 | | 10/15 | 66.70 |
| 10-6 | i.n.-s.q. | " | $6.1 \times 10^6$ | 5/0 | 4/1 | 1/3 | 1/0 | 1/0 | 1/0 | 1/0 | | 1/5 | 20 |
| 1-17 | " | " | $2.25 \times 10^6$ | 5/0 | 5/0 | 4/1 | 4/0 | 4/0 | 4/0 | 4/0 | | 4/5 | 80 |
| 1-20 | " | " | $6.75 \times 10^6$ | 5/0 | 4/1 | 1/3 | 1/0 | 1/0 | 1/0 | 1/0 | | 1/5 | 20 |
| total | " | " | $5.03 \times 10^6$ | 15/0 | 13/2 | 6/7 | 6/0 | 6/0 | 6/0 | 6/0 | | 6/15 | 40 |
| 10-6 | controls | " | $6.1 \times 10^6$ | 4/0 | 1/3 | 0/1 | | | | | | 0/40 | 0 |
| 1-17 | " | " | $2.25 \times 10^6$ | 4/0 | 3/1 | 2/1 | 0/2 | | | | | 0/4 | 0 |
| 1-20 | " | " | $6.75 \times 10^6$ | 5/0 | 3/2 | 1/2 | 0/1 | | | | | 0/5 | 0 |
| total | " | " | $5.03 \times 10^6$ | 13/0 | 7/6 | 3/4 | 0/3 | | | | | 0/13 | 0 |

[a]CFU given in "total" represents the mean out of the CFU of the 3 experiments (SEM = $1.99 \times 10^6$)

Virji et al. (1993, *Mol. Microbiol.* 10: 1013–1028) presented strong evidence (carbohydrate detection of blotted pilin and chemical removal of sugars) that Neisseria meningitidis pilin is glycosylated. Results presented in this paper suggest that pilin from P. aeruginosa 1244 also is glycosylated. The composition of the pilin-associated material remains to be determined, however several candidates, including the acidic moieties of the lipopolysaccharide core, alginic acid subunits, as well as other acidic elements or phosphorylated compounds, must be considered. Limitations of SDS-PAGE prevent reliable molecular weight determinations of glycosylated proteins, a test which must await the use of a more accurate technique such as mass spectrometry. Linkage of glycosylated proteins is usually via the reducing end of an oligosaccharide sugar through an O- or N-linkage to the hydroxyl group of serine (or threonine) or the amide group of asparagine (Montreuil et al., 1986, In *Carbohydrate Analysis, a Practical Approach*, pp. 143–204. Edited by M. F. Chaplin & J. F. Kennedy. Oxford: IRL Press). The residues in the region of N-linked moieties have the characteristic consenus sequence N-X-S (or T). While this sequence may be found in the N. meningitidis pilin primary structure (Virji et al., 1993), it is absent in *P. aeruginosa* strain 1244 pilin, suggesting the presence of an N-linkage, a different sequence specificity, or the utilization of an alternative method of attachment. Clearly much work remains in the characterization of this pilinassociated material.

Previous work (Frost & Paranchych, 1977; Paranchych et al., 1979) has indicated that pili from *P. aeruginosa* strains PAO and PAK contained no sugar residues. Since the primary structure of pili from strain 1244 is distinctive when compared to those of strains PAO and PAK (Castric & Deal, 1994), pilus modification may represent a strain difference. *P. aeruginosa* strains producing pili antigenically related to those of strain 1244 are common among clinical isolates (Castric & Deal, 1994). Thus, pilin glycosylation by this bacterium could be useful in clinical identification. Likewise, demonstration of the presence of the pilO gene could be of diagnostic value.

Since the absence of glycosylation seems to have no effect on either the formation of pilus fibres or extension and retraction of these fibres (as measured by bacteriophage sensitivity and twitching motility), the function of this modification is unclear. Because all pilin monomers appear to be modified [this must include both the pilin membrane pool (Watts et al., 1982c, *J. Bacteriol*. 152: 687–691) as well as pilus fibres), these glycoproteins must contribute greatly to the overall cell surface negativity. Bacterial avoidance of phagocytosis through inhibition of attachment has been well documented (Densen & Mandell, 1980, *Rev. Infect. Dis.* 2: 817–838). Diminished phagocytosis by neutrophils because of electrostatic repulsion has been demonstrated both by streptococcal M protein (Fischetti, 1989, *Clin. Microbiol. Rev.* 2: 285–314) and the pili of Neisseria gonorrhoeae (Heckels et al., 1976, *J. Gen. Microbiol.* 76: 359–364). Such a mechanism could also benefit *P. aeruginosa* when growing saprophytically where the avoidance of phagocytic amoebae could be an important survival mechanism.

Specific recognition by the pili allows attachment of the pathogen to host cells containing the proper receptors (Baker, 1993, In *Pseudomonas aeruginosa, the Opportunist: Pathogenesis and Disease*, pp. 7–24. Edited by R. B. Fick. Boca Raton: CRC Press; Heckels et al., 1976). The acidic modification might stabilize this attachment through the formation of salt bridges once specific binding had occurred. Alternately pilin glycosylation may be involved in specific or nonspecific adhesion to the host cell which is independent of pilin protein-mediated attachment. Adhesion studies utilizing PilO+ and PilO− variants of *P. aeruginosa* strain 1244, as well as glycosylated and nonglycosylated pili, will be required to clarify these points.

The genetic evidence presented in this paper relates the presence of pilin glycosylation to a functioning pilO gene indicates that this process has a specific cellular role. This is strongly supported by the findings that the pilO gene is part of the pilA transcriptional unit. Although the pilA and pilO genes, along with a tRNA$^{thr}$ gene, are present in the form of an operon, two major transcription products are generated (an individual pilA message and apilA/pilO/tRNA$^{thr}$ transcript) which are present in a ratio of about one hundred to one. Such results would not be unexpected as pilin is a major cell protein, while PilO would likely be required in only catalytic or regulatory amounts. The difference in transcription levels could be the result of premature termination of message synthesis or relative instability of the transcript corresponding to the pilO region. The role of translation efficiency should also be considered a factor in differential gene expression since the beginning of the pilO message contains a short loop region which includes the start codon. Such a structure has been suggested to be able to significantly reduce translation (Gold, 1988, *Annu. Rev. Riochem.* 57: 199–233), and may function to further control expression of a gene coding for a product required in small amounts when it shares a promoter with a gene coding for a product needed in large amounts.

The pilO gene product is predicted to code for a protein with a molecular weight of 50,862 using as start codon the ATG beginning at position 729 (FIG. 1). Hydropathy profile (Kyte & Doolittle, 1982, *J. Mol. Biol.* 157: 105–132) of the primary structure indicates that PilO contains nine hydrophobic regions which are flanked by clusters of charged residues. Secondary structure prediction (Chou & Fassman, 1974, *Biochemistry* 13: 211–221) suggests that large portions, of these hydrophobic regions are composed of β-structure which are of adequate length to span the 3.0 nm membrane lipid core. Positively charged residues flanking the hydrophobic segments could be expected to stabilize this structure through ionic interaction with membrane phospholipids, while charged and polar residues in these regions would promote a surface solvent interaction on both sides of a membrane. Although the location of PilO has not been demonstrated, the high degree of hydrophobicity within the predicted transmembrane regions suggests that it resides in the cytoplasmic membrane. This location would be ideal if PilO functions catalytically on the periplasm side of the cytoplasmic membrane to transfer carrier lipid-bound oligosaccharide subunits to emerging pilin monomers.

What is claimed is:

1. A multivalent vaccine against Gram-negative bacterial infections comprising heterologously glycosylated pili from *Pseudomonas aeruginosa* to which are covalently attached the O-antigen repeating units of different strains or species of Gram-negative bacteria capable of eliciting a protective response against Gram-negative bacterial infections in a pharmaceutically acceptable excipient, in a pharmaceutically acceptable amount.

2. The vaccine according to claim 1 wherein said *Pseudomonas aeruginosa* is *Pseudomonas aeruginosa* 1244.

3. A multivalent vaccine against Gram-negative bacterial infections comprising heterologously glycosylated pili from *Pseudomonas aeruginosa* to which are covalently attached the O-antigen repeating unit of different strains or species of Gram-negative bacteria wherein said pili are produced by (i) introducing a vector, pPAC46, containing pilA, the *Pseudomonas aeruginosa* pilin structural gene, and pilO, the gene from *Pseudomonas aeruginosa* coding for the protein responsible for attachment of the O-antigen repeating unit to the pilin subunit, into said Gram-negative bacteria such that pilA and pilO are expressed and are capable of adding the O-antigen repeating unit of said Gram negative bacteria to said pilin; and (ii) growing the bacteria on broth or solid medium and purifying pili produced.

4. The vaccine according to claim 3, wherein said vaccine is suitable for mucosal administration.

5. The vaccine according to claim 4, wherein said vaccine is suitable for intranasal administration.

6. A multivalent vaccine against Gram-negative bacterial infections comprised of a single *Pseudomonas aeruginosa* pilus type to which is covalently attached the O-antigen repeating unit of a plurality of heterologous strains and species of Gram-negative bacteria.

* * * * *

SEQUENCE LISTING (1) GENERAL INFORMATION:

(iii) NUMBER OF SEQUENCES:  4

(2) INFORMATION FOR SEQ ID NO:1:

(i) SEQUENCE CHARACTERISTICS:
      (A) LENGTH: 1386 base pairs
      (B) TYPE: Nucleic acid
      (C) STRANDEDNESS:Double (D) TOPOLOGY: Linear (ii) SEQUENCE DESCRIPTION: SEQ ID NO:1:

| | | | | |
|---|---|---|---|---|
| ATGCGAATTT | GGCTAGCCTG | GGAAAGGATG | GGTAGGGCGT | 40 |
| CGCGTACTAT | TCTATTATTG | CTGATAAGTA | TTCTTCTGCT | 80 |
| TTCTCCCGTT | GTTTACTGCG | GGGTTTCCAA | GAACTGGCAT | 120 |
| GATCAGCAGC | GAATACTCCA | ATTGGTGGTG | TTGAGTGGAT | 160 |
| CGTCACTCCT | GCTGCTCTTT | TCTTCTCGTC | TGTCATTTGC | 200 |
| CAGAAGGATG | GTTCAGGTAA | CACTTTTGGT | TATCTTGGGT | 240 |
| CTAGGCAGCG | TTTCCGCATT | TCTCTCCGCC | AATCCTTCCT | 280 |
| GGGCATTCAA | GGAATGGTCG | GTATTCGCCG | GCCTGATGCT | 320 |
| GTTTTCCTTC | AATATATCCG | CCAGCCCAGA | GTGGGTTCGC | 360 |
| CGTATCGCCC | TCTGGGGGT | GGTCGTGTTG | GGAGGGTTCT | 400 |
| TCTGCTACCA | GTTCCTGCTT | TCCTATCTCG | CGGCCTTCGT | 440 |
| CAGCGGACTC | CGTGAGTTGA | ATCCCAGGGT | TTTGCTCAGC | 480 |
| GGCTTTTCCA | ACGTCCGGAC | CATGGGGCAG | TTCCAGGCCA | 520 |
| TGCTGCTGCC | GCTGATGGCT | GCGCTGGGGT | TGTACCTACG | 560 |
| AGAGACCGGG | CGGTTCAGAC | TGTCCTGGCT | TGTCATGCTG | 600 |
| CTGCTGGCCA | TCCAATGGTG | CATCTCCTTC | GCCTTGGCTG | 640 |
| GACGCGGGCT | CTGGTTGGGT | TTCGCCGTCG | CGCATCTCGC | 680 |
| GCTTTGCTGG | ATCGGCCCCG | TGGGGCGCCG | CTTTTTGATC | 720 |
| GTCCAGTTGT | CCGCGGCATT | CGTCGGGTTG | GCGCTCTATT | 760 |
| TCCTGTTAAT | GGTTGCCTTG | CCGACCTGGC | TCGGTATCGA | 800 |
| CATGACCCTC | ATGTCCGGTA | TGCGCAGTGG | TCTGTCTCTG | 840 |
| CGCGACGTGT | TGTGGCGAGA | TGCCTGGGGC | ATGTTCGTAG | 880 |
| CCCATCCTTT | GCTTGGGGTC | GGGCCCATGC | ATTTCTCGGC | 920 |
| GGTGCCGAAC | AGCGTCGGTG | CCCACCCGCA | CCAGATGCTG | 960 |
| CTGCAGTGGT | TCGCTGAATG | GGGCGGGGCC | GCTGGCCTTC | 1000 |
| TGGTGGTTGG | ACTGATGACC | CTTGGTCTGC | TTCGCGGCGC | 1040 |
| GCGTTACCTG | CGTGAACAGG | GCGATCCGAT | GGACGCCGGA | 1080 |
| CTGTGGCTGG | CCCTCGTTTC | GGTCCTGGTC | TTGGCCCAGG | 1120 |
| TGGACGGCGT | GTTCGTCATG | CCCTTCACCC | AGACCGTATT | 1160 |
| GGCCTTGCTG | GTAGGCATCG | CCATGGCGCG | CTGGTCGAAG | 1200 |
| CCGGTCGTGC | CGTCCCCCGC | ACAGCGCTGG | CTCTGTCGGG | 1240 |
| GCCTGGCTGT | CGTTGTCATT | GTCGTGCTGG | GGCGCGTGCT | 1280 |
| GCTGCTCGAG | GTGCCGGGGC | TGACCGCGGC | CGAGGAGCGC | 1320 |
| TACCTGGAAA | TCCACGGCGG | CGGTGAGGCG | CCACGTTTCT | 1360 |
| GGATTCAGGG | TTGGATTCCC | ATGTGA | | 1386 |

(2) INFORMATION FOR SEQ ID NO:2:

(i) SEQUENCE CHARACTERISTICS:
(A) LENGTH:461 amino acids (B) TYPE: amino acids
(C) STRANDEDNESS: single
(D) TOPOLOGY: Circular (ii) SEQUENCE DESCRIPTION: SEQ ID NO:2:

```
Met Arg Ile Trp Leu Ala Trp Glu Arg Met Gly Arg Ala Ser Arg
             5                  10                  15

Thr Ile Leu Leu Leu Leu Ile Ser Ile Leu Leu Leu Ser Pro Val
            20                  25                  30

Val Tyr Cys Gly Val Ser Lys Asn Trp His Asp Gln Gln Arg Ile
            35                  40                  45

Leu Gln Leu Val Val Leu Ser Gly Ser Ser Leu Leu Leu Leu Phe
            50                  55                  60

Ser Ser Arg Lys Ser Phe Ala Arg Arg Met Val Gln Val Thr Leu
            65                  70                  75

Leu Val Ile Leu Gly Leu Gly Ser Val Ser Ala Phe Leu Ser Ala
            80                  85                  90

Asn Pro Ser Trp Ala Phe Lys Glu Trp Ser Val Phe Ala Gly Leu
            95                 100                 105

Met Leu Phe Ser Phe Asn Ile Ser Ala Ser Pro Glu Trp Val Arg
           110                 115                 120

Arg Ile Ala Leu Trp Gly Val Val Leu Gly Gly Phe Phe Cys
           125                 130                 135

Tyr Gln Phe Leu Leu Ser Tyr Leu Ala Ala Phe Val Ser Gly Leu
           140                 145                 150

Arg Glu Leu Asn Pro Arg Val Leu Leu Ser Gly Phe Ser Asn Val
           155                 160                 165

Arg Thr Met Gly Gln Phe Gln Ala Met Leu Leu Pro Leu Met Ala
           170                 175                 180

Ala Leu Gly Leu Tyr Leu Arg Glu Thr Gly Arg Phe Arg Leu Ser
           185                 190                 195

Trp Leu Val Met Leu Leu Ala Ile Gln Trp Cys Ile Ser Phe
           200                 205                 210

Ala Leu Ala Gly Arg Gly Leu Trp Leu Gly Phe Ala Val Ala His
           215                 220                 225

Leu Ala Leu Cys Trp Ile Gly Pro Val Gly Arg Arg Phe Leu Ile
           230                 235                 240

Val Gln Leu Ser Ala Ala Phe Val Gly Leu Ala Leu Tyr Phe Leu
           245                 250                 255

Leu Met Val Ala Leu Pro Thr Trp Leu Gly Ile Asp Met Thr Leu
           260                 265                 270

Met Ser Gly Met Arg Ser Gly Leu Ser Leu Arg Asp Val Leu Trp
           275                 280                 285

Arg Asp Ala Trp Gly Met Phe Val Ala His Pro Leu Leu Gly Val
           290                 295                 300

Gly Pro Met His Phe Ser Ala Val Pro Asn Ser Val Gly Ala His
           305                 310                 315

Pro His Gln Met Leu Leu Gln Trp Phe Ala Glu Trp Gly Gly Ala
           320                 325                 330

Ala Gly Leu Leu Val Val Gly Leu Met Thr Leu Gly Leu Leu Arg
           335                 340                 345

Gly Ala Arg Tyr Leu Arg Glu Gln Gly Asp Pro Met Asp Ala Gly
           350                 355                 360

Leu Trp Leu Ala Leu Val Ser Val Leu Val Leu Ala Gln Val Asp
```

```
                   365                 370                 375
Gly Val Phe Val Met Pro Phe Thr Gln Thr Val Leu Ala Leu Leu
               380                 385                 390
Val Gly Ile Ala Met Ala Arg Trp Ser Lys Pro Val Val Pro Ser
               395                 400                 405
Pro Ala Gln Arg Trp Leu Cys Arg Gly Leu Ala Val Val Ile
               410                 415                 420
Val Val Leu Gly Arg Val Leu Leu Leu Glu Val Pro Gly Leu Thr
               425                 430                 435
Ala Ala Glu Glu Arg Tyr Leu Glu Ile His Gly Gly Gly Glu Ala
               440                 445                 450
Pro Arg Phe Trp Ile Gln Gly Trp Ile Pro Met
               455                 460

(2) INFORMATION FOR SEQ ID NO:3:

(i) SEQUENCE CHARACTERISTICS:
        (A) LENGTH: 8 amino acids
        (B) TYPE:   amino acids
        (C) STRANDEDNESS: single
        (D) TOPOLOGY: Circular (xi) SEQUENCE DESCRIPTION: SEQ ID NO:3:

Thr Val Glu Leu Val Ala Thr Leu
                 5

(2) INFORMATION FOR SEQ ID NO:4:

(i) SEQUENCE CHARACTERISTICS:
        (A) LENGTH:  17 amino acids
        (B) TYPE:   amino acids
        (C) STRANDEDNESS: single
        (D) TOPOLOGY: Circular (xi) SEQUENCE DESCRIPTION: SEQ ID NO:4:

Thr Pro Thr Ala Trp Lys Pro Asn Tyr Ala Pro Ala Asn Cys Pro
                 5                  10                  15
Lys Ser
```